United States Patent [19]

Bundy

[11] 4,060,534
[45] Nov. 29, 1977

[54] 9-DEOXY-9-METHYLENE-PGF COMPOUNDS

[75] Inventor: Gordon L. Bundy, Portage, Mich.

[73] Assignee: The Upjohn Company, Kalamazoo, Mich.

[21] Appl. No.: 682,848

[22] Filed: May 4, 1976

Related U.S. Application Data

[60] Continuation-in-part of Ser. No. 651,622, Jan. 23, 1976, Pat. No. 4,021,467, which is a division of Ser. No. 556,768, March 10, 1975, Pat. No. 3,950,363.

[51] Int. Cl.$^2$ .............................................. C07C 177/00
[52] U.S. Cl. ............................. 260/408; 260/410.9 R; 260/413; 260/514 D; 560/121
[58] Field of Search ....... 260/408 D, 514 D, 514 CA, 260/410.9 R, 408, 413

[56] References Cited

U.S. PATENT DOCUMENTS 3,931,299  1/1976  Strike .................................. 260/514

*Primary Examiner*—Robert Gerstl
*Attorney, Agent, or Firm*—Robert A. Armitage

[57] ABSTRACT

This invention comprises certain analogs PGE or 11-deoxy-PGE compounds in which the carbonyl at C-9 is replaced by methylene. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

226 Claims, No Drawings

9-DEOXY-9-METHYLENE-PGF COMPOUNDS

CROSS REFERENCE TO RELATED APPLICATIONS

The present application is a continuation-in-part of Ser. No. 651,622 filed Jan. 23, 1976, now issued as U.S. Pat. No. 4,021,467 which is a division of Ser. No. 556,768, filed Mar. 10, 1975, now issued as U.S. Pat. No. 3,950,363.

BACKGROUND OF THE INVENTION

This invention provides novel compositions of matter. This invention further provides novel processes for producing these compositions of matter. This invention further provides novel chemical intermediates useful in the above processes.

Particularly this invention provides novel analogs of some of the known PGE compounds which differ from corresponding known PGE compounds in that these prostaglandin analogs have a methylene at C-9.

The known PGE compounds include e.g. prostaglandin $E_1$ (PGE$_1$), prostaglandin $E_2$ (PGE$_2$), prostaglandin $E_3$ (PGE$_3$), and dihydroprostaglandin $E_1$ (dihydro-PGE$_1$).

Each of the above mentioned known PGE compounds is a derivative of prostanoic acid which has the following structure and carbon atom numbering

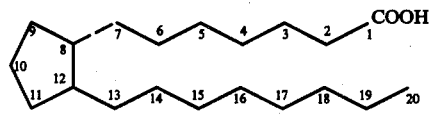

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

PGE$_1$ has the following structure:

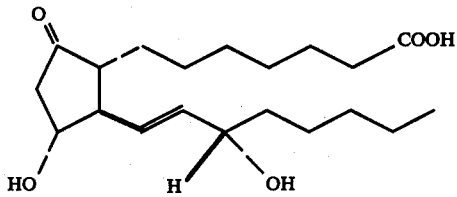

PGE$_2$ has the following structure:

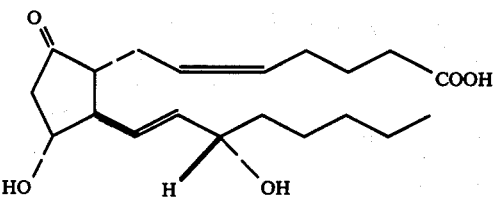

PGE$_3$ has the following structure:

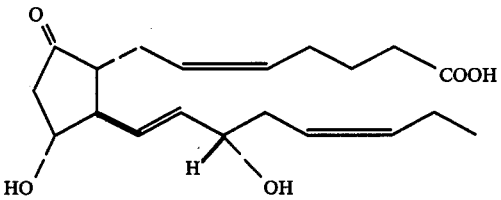

Dihydro-PGE$_1$ has the following structure:

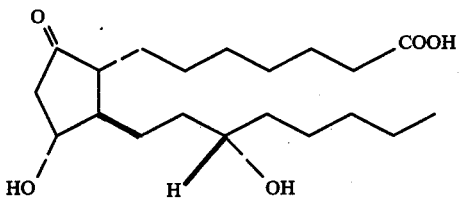

In the above formulas, as well as in the formulas hereiafter given, broken line attachments to the cyclopentane ring indicate substitutents in alpha configuration i.e., below the plane of the cyclopentane ring. Heavy solid line attachments to the cyclopentane ring indicate substituents in beta configuration, i.e., above the plane of the cyclopentane ring. The use of wavy lines (∼) herein will represent attachment of substitu-lines in either the alpha or beta configuration or attachment in a mixture of alpha and beta configurations.

The side-chain hydroxy at C-15 in the above formulas is in S configuration. See, Nature 212, 38 (1966) for discussion of stereochemistry of the prostaglandins. Expressions such as C-9, C-15, and the like, refer to the carbon atom in the prostaglandin analog which is in the position corresponding to the position of the same number in prostanoic acid.

Molecules of the known prostaglandins each have several centers of asymmetry, and can exist in racemic (optically inactive) form and in either of the two enantiomeric (optically active) forms, i.e. the dextrorotatory and levorotatory forms. As drawn, the above formulas each represent the particular optically active form of the prostaglandin as is obtained from mammalian tissues, for example, sheep vesicular glands, swine lung, or human seminal plasma, from carbonyl and/or double bond reduction of the prostaglandin so obtained. See, for example, Bergstrom et al., cited above. The mirror image of each of these formulas represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin. For convenience hereinafter, use of the term, prostaglandin or "PG" will mean the optically active form of that prostaglandin thereby referred to with the same absolute configuration as PGE$_1$ obtained from mammalian tissues. When reference to the racemic form of one of those prostaglandins is intended, the word "racemic" or "dl" will precede the prostaglandin name.

The term "prostaglandin-type" (PG-type) product, as used herein, refers to any cyclopentane derivative which is useful for at least one of the same pharmacological purposes as the prostaglandins, as indicated herein.

The term prostaglandin-type intermediate, as used herein, refers to any cyclopentane derivative useful in preparing a prostaglandin-type product.

The formulas, as drawn herein, which depict a prostaglandin-type product or an intermediate useful in preparing a prostaglandin-type product, each represent the particular stereoisomer of the prostaglandin-type product which is of the same relative stereochemical configuration as a corresponding prostaglandin obtained from mammalian tissues, or the particular stereoisomer of the intermediate which is useful in preparing the above stereoisomer of the prostaglandin-type product.

The term "prostaglandin analog", as used herein, represents that stereoisomer of a prostaglandin-type product which is of the same relative stereochemical configuration as a corresponding prostaglandin obtained from mammalian tissues or a mixture comprising that stereoisomer and the enantiomer thereof. In particular, where a formula is used to depict a prostaglandin-type compound herein, the term prostaglandin analog refers to the compound of the formula, or a mixture comprising that compound and the enantiomer thereof.

The various PGE's named above, their esters, acylates and pharmacologically acceptable salts, are extremely potent in causing various biological responses. For that reason, these compounds are useful for pharmacological purposes. See, for example, Bergstrom et al., Pharmacol. Rev. 20, 1 (1968) and references cited therein.

For the PGE compounds these biological responses include:

a. decreasing blood pressure (as measured, for example, in anesthetized, pentolinium-treated rats);
b. stimulating smooth muscle (as shown by tests, for example, on guinea pig ileum, rabbit duodenum, or gerbil colon);
c. effecting lipolytic activity (as shown by antagonism of epinephrine induced release of glycerol from isolated rat fat pads);
d. inhibiting gastric secretion and reducing undesirable gastrointestinal effects from systematic administration of prostaglandin synthetase inhibitors;
e. controlling spasm and facilitating breathing in asthmatic conditions;
f. decongesting nasal passages;
g. decreasing blood platelet adhesion (as shown by platelet to glass adhesiveness) and inhibiting blood platelet aggregation and thrombus formation induced by various physical stimuli (e.g., arterial injury) or chemical stimuli (e.g., ATP, ADP, serotinin, thrombin, and collagen);
h. affecting the reproductive organs of mammals as labor inducers, abortifacients, cervical dilators, regulators of the estrus, and regulators of the menstrual cycle; and
j. accelerating growth of epidermal cells and keratin in animals.

Because of these biological responses, these known PGE compounds are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

The PGE compounds cited above as hypotensive agents are useful to reduce blood pressure in mammals, including man. For this purpose, the compounds are administered by intravenous infusion at the rate about 0.01 to about 50 μg. per kg. of body weight per minute or in single or multiple doses of about 25 to 500 μg. per kg. of body weight total per day.

The PGE compounds cited above as extremely potent in causing stimulation of smooth muscle are also highly active in potentiating other known smooth muscle stimulators, for example, oxytocic agents, e.g., oxytocin, and the various ergot alkaloids including derivatives and analogs thereof. Therefore, these compounds for example, are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the prostaglandin is administered by intravenous infusion immediately after abortion or delivering at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g. diabetes mellitus, vascular diseases, and hyperthyroidism. bicarbonate, The PGE compounds as cited above as useful in mammals including man and certain useful animals, e.g., dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for that purpose by concomitant administration of the prostaglandin and the antiinflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including PGE$_1$, PGE$_2$, PGE$_3$, 13,14-dihydro-PGE$_1$, and the corresponding 11-deoxy-PGE and PGA compounds. Prostaglandins are useful, for example, in reducing the undesirable gastointestinal effects resulting from systemic administration of indomethacin, phenylbutazone and aspirin. These are substances specifically mentioned in Partridge et al. as non-steroidal, anti-inflammatory agents. These are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally. Further, the prostaglandin can be conveniently administered orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

The PGE compounds so cited above as useful in the treatment of asthma, are useful, for example, as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g., orally in the form of tablets, capsules, or liquids; rectally in the form of suppositories; parenterally; subcutaneously; or intramuscularly; with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight and condition of the patient and on the frequency and route of administration. For the above use these prostaglandins can be combined advantageously with other anti-asthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

The PGE compounds cited above as useful in mammals, including man, as nasal decongestants are used for this purpose, in a dose range of about 10 $\mu$g. to about 10 mg. per ml. of a pharmacologically suitable liquid vehicle or as an aerosol spray, both for topical application.

The PGE compounds so cited above are useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dosage depending on the age, weight, and condition of the patient or animal, and on the frequency and route of administration.

These PGE compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purposes, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

The PGE compounds cited above as useful in place of oxytocin to induce labor are used in pregnant female animals including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks postmature and natural labor has not started, or 12 to 60 hours after the membranes have ruptured and natural labor has not yet started. An alternative route of administration is oral.

These compounds are further useful for controlling the reproductive cycle in menstruating female mammals, including humans. By the term menstruating female mammals is meant animals which are mature enough to menstruate, but not so old that regular menstruation has ceased. For that purpose the prostaglandin is administered systemically at a dose level in the range of 0.01 mg. to about 20 mg. per kg. of body weight of the female mammal, advantageously during a span of time starting approximately at the time of ovulation and ending approximatly at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the prostaglandin is administered locally or systemically.

The PGE compound, for example, is administered orally or vaginally at doses of about 5 to 500 mg. per treatment of an adult female human, with from one to five treatments per 24 hour period. Alternatively the prostaglandin is administered intramuscularly or subcutaneously at doses of about one to 25 mg. per treatment. The exact dosages for these purposes depend on the age, weight, and condition of the patient or animal.

These compounds are further useful in domestic animals as an abortifacient (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin is injected or applied in a feed at doses of 0.1-100 mg. per animal and may be combined with other agents such as steroids. Dosing schedules will depend on the species treated. For example, mares are given the prostaglandin 5 to 8 days after ovulation and return to estrus. Cattle, are treated at regular intervals over a 3 week period to advantageously bring all into estrus at the same time.

The PGE compounds cited above as promoters and accelerators of growth of epidermal cells and keratin are useful in animals, including humans, useful domestic animals, pets, zoological specimens, and laboratory animals for this purpose. For this reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For the above purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separately or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 μg. per ml. of the prostaglandin. Especially for topical use, these prostaglandins are useful in combination with antibiotics, for example, gentamycin, neomycin, polymixin, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

9,11-Dideoxy-9-methylene-$PGF_1$ and $PGF_2$ are described in U.S. Pat. No. 3,931,299.

SUMMARY OF THE INVENTION

The present invention provides:
a prostaglandin analog of the formula

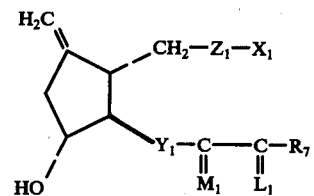

wherein $Y_1$ is trans-CH=CH—, —C≡C—, or —$CH_2Ch_2$—;
wherein $M_1$ is

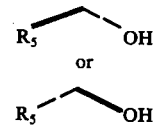

wherein $R_5$ is hydrogen or methyl;
wherein $L_1$ is

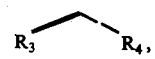

-continued

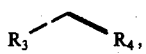

or a mixture of

and
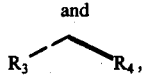

wherein $R_3$ and $R_4$ are hydrogen, methyl, or fluoro, being the same or different, with the proviso that one of $R_3$ and $R_4$ is fluoro only when the other is hydrogen or fluoro;
wherein $Z_1$ is
1. cis—$CH$=$CH$—$CH_2$—$(CH_2)_g$—$CH_2$—,
2. cis—$CH$=$CH$—$CH_2$—$(CH_2)_g$—$CF_2$,
3. cis—$CH_2$—$CH$=$CH$—$(CH_2)_g$—$CH_2$—,
4. —$(CH_2)_3$—$(CH_2)_g$—$CH_2$—,
5. —$(CH_2)_3$—$(CH_2)_g$—$CF_2$—,
6. —$CH_2$—$O$—$CH_2$—$(CH_2)_g$—$CH_2$—,
7. —$C$≡$CH_2$—$(CH_2)_g$—$CH_2$—,
8. —$CH_2$—$C$≡$C$—$(CH_2)_g$—$CH_2$—,

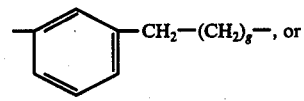

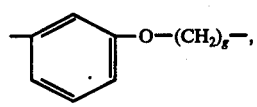

wherein $g$ is one, 2, or 3;
wherein $R_7$ is
1. —$(CH_2)_m$—$CH_3$,

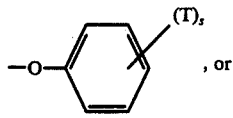

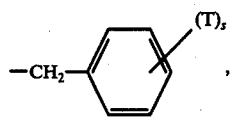

wherein $m$ is one to 5, inclusive, T is chloro, fluoro, trifluoromethyl, alkyl of one to 3 carbon atoms, inclusive, or alkoxy of one to 3 carbon atoms, inclusive, and $s$ is zero, one, 2, or 3, the various T's being the same or different, with the proviso that not more than two T's are other than alkyl, with the further proviso that $R_7$ is

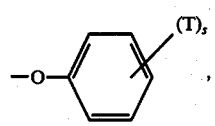

wherein T and $s$ are as defined above, only when $R_3$ and $R_4$ are hydrogen or methyl, being the same or different; and wherein $X_1$ is
1. —$COOR_1$; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two or three chloro or alkyl of one to 3 carbon atoms, inclusive, or a pharmacologically acceptable cation,
2. —$CH_2OH$, or
3. —$CH_2NL_2L_3$, wherein $L_2$ and $L_3$ are hydrogen, alkyl of one to 4 carbon atoms, inclusive, or —$COOR_1$, wherein $R_1$ is as defined above;

and the 1,11- or 1,15-lactones thereof.

The novel prostaglandin analogs of this invention, are all named 9-deoxy-9-methylene-PGF-type compounds by mixture of this cyclopentane ring structure;

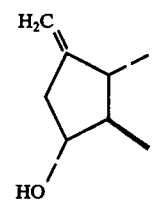

(9)

The present invention further discloses the preparation of novel 9,11-deoxy-9-methylene-PGF-type compounds, exhibiting the following cyclopentane ring structure:

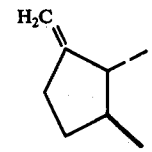

(10)

Those prostaglandin analogs herein wherein $Z_1$ is cis—$CH$=$CH$—$CH_2$—$(CH_2)_g$-$CH_2$— or cis—$CH$=•$CH$—$CH_2$—$(CH_2)_g$—$CF_2$— are named as "$PG_2$" compounds. The latter compounds are further characterized as "2,2-difluoro" PG-type compounds. When $g$ is 2 or 3, the prostaglandin analogs so described are "2a-homo" or "2a,2b-dihomo" compounds, since in this event the carboxy terminated side chain contains 8 or 9 carbon atoms, respectively, in place of the 7 carbon atoms contained in $PGE_1$. These additional carbon atoms are considered as though they were inserted between the C-2 and C-3 positions. Accordingly, these additional carbon atoms are referred to as C-2a and C-2b, counting from the C-2 to the C-3 position.

Further when $Z_1$ is —$(CH_2)_3$—$(CH_2)_g$—$CH_2$— or —$(CH_2)_3$—$(CH_2)_g$—$CF_2$, wherein $g$ is as defined above, the compounds so described are "$PG_1$" compounds. When $g$ is 2 or 3, the "2a-homo" and "2a,2-dihomo" compounds are described as is discussed in the preceding paragraph.

When $Z_1$ is —$CH_2$—$O$—$CH_2$—$(CH_2)_g$—$CH_2$— the compounds so described are named as "5-oxa-$PG_1$" compounds. When $g$ is 2 or 3, the compounds so described are "2a-homo" or "2a,2b-dihomo" compounds, respectively, as discussed above.

When $Z_1$ is —$C$≡$C$—$CH_2$—$(CH_2)_g$—$CH_2$— wherein $g$ is as defined above, the compounds so described are named as "5,6-didehydro-$PG_2$" compounds. When $g$ is 2 or 3, the compounds so described are additionally characterized as "2a-homo" or "2a-dihomo" compounds, respectively, as is discussed above.

When $Z_1$ is cis—$CH_2$—CH=CH—$(CH_2)_g$—$CH_2$—, wherein g is as defined above, the compounds so described are named "cis-4,5-didehydro-$PG_1$" compounds. When g is 2 or 3, the compounds so described are further characterized as "2a-homo" or "2a, 2b-dihomo" compounds, respectively, as discussed above.

For the novel compounds of this invention wherein $Z_1$ is

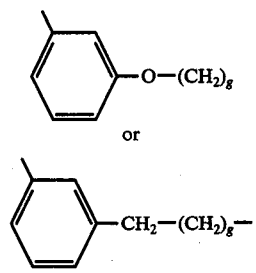

there are described, respectively, 3-oxa-3,7-inter-m-phenylene-4,5,6-trinor- or 3,7-inter-m-phenylene-4,5,6-trinor-PG-type compounds, when g is 1. When g is 2 or 3, the above compounds are additionally described as "2a-homo" or "2a,2b-dihomo" PG-type compounds, respectively.

The novel prostaglandin analogs of this invention which contain a —$CH_2CH_2$— or —C≡C— moiety at the C-13 to C-14 position, and are accordingly, referred to as "13,14-dihydro" or "13,14-didehydro" compounds, respectively.

When $R_7$ is —$(CH_2)_m$—$CH_3$, wherein m is as defined above, the compounds so described are named as "19,20-dinor," "20-nor", "20-methyl", or "20-ethyl" compounds when m is one, 2, 4, or 5, respectively.

When $R_7$ is

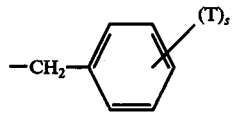

wherein T and s are as defined above, the compounds so described are named as "17-phenyl-18,19,20-trinor" compounds, when s is 0. When s is one, 2, or 3, the corresponding compounds are named as "17-(substituted phenyl)18,19,20-trinor" compounds.

When $R_7$ is

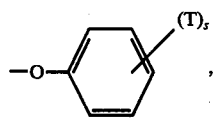

wherein T and s are as defined above, and neither $R_3$ nor $R_4$ is methyl, the compounds so described are named as "16-phenoxy-17,18,19,20-tetranor" compounds, when s is zero. When s is one, 2, or 3, the corresponding compounds are named as "16-(substituted phenoxy)-17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenoxy or 16-(substituted phenoxy)-18,19,20-trinor" compounds or "16-methyl-16-phenoxy- or 16-(substituted phenoxy)-18,19,20-trinor" compounds, respectively.

When at least one of $R_3$ and $R_4$ is not hydrogen then (except for the 16-phenoxy compounds discussed above) there are described the "16-methyl" (one and only one of $R_3$ and $R_4$ is methyl), and "16,16-dimethyl" ($R_3$ and $R_4$ are both methyl), "16-fluoro" (one and only one of $R_3$ and $R_4$ is fluoro), "16,16-difluoro" ($R_3$ and $R_4$ are both fluoro) compounds. For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When $R_5$ is methyl, the compounds so described are named as "15-methyl" compounds.

When $X_1$ is —$CH_2OH$, the compounds so described are named as "2-decarboxy-2-hydroxymethyl" compounds.

When $X_1$ is —$CH_2NL_2L_3$, the compounds so described are named as "2-decarboxy-2-aminomethyl or 2-(substituted amino)methyl" compounds.

There is further provided by this invention both epimeric configurations of the hydroxy at C-15. As discussed herein, $PGE_1$, as obtained from mammalian tissues, has the "S" configuration at C-15. Further, as drawn herein $PGE_1$, as obtained from mammalian tissues, has the 15-hydroxy moiety in the "alpha" configuration.

For the 13,14-dihydro or 13,14-didehydro derivative of $PGE_1$ as obtained from mammalian tissues, the S configuration at C-15 represents the α-hydroxy configuration, using the convention by which the side chains of the novel prostagland analogs of this invention are drawn herein, as indicated above. Further, (15R)-$PGE_1$, by the convention used for drawing the prostaglandins herein, has the 15-hydroxy substituent in the beta configuration. The corresponding (15R)-13,14-dihydro- or 13,14-didehydro-$PGE_1$ compound, drawn using the convention herein for the representation of the novel prostagland analogs of this invention, likewise has the 15-hydroxy in the beta configuration. Thus, the novel prostaglandin analogs of this invention wherein the 15-hydroxy moiety has the same absolute configuration as (15R)-13,14-dihydro- or 13,14-didehydro-$PGE_1$ at C-15 will be named "15-epi" compounds. When the designation "15-epi" is absent, those compounds wherein the configuration of the 15-hydroxy or 15-methoxy is the same as the absolute configuration of 15(S)-13,14-dihydro- or 13,14-didehydro-$PGE_1$are represented, i.e. the 15α-hydroxy configuration.

Accordingly, as indicated by the preceding paragraphs, the novel PG analogs disclosed herein are named according to the system described in Nelson, N. A., J. Med. Chem. 17, 911 (1974).

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalky, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of

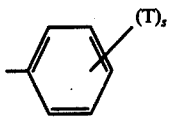

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)-ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-,2,3,6-, or 2,4,5)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)di-fluorophenyl, (o-, m-, or p-)-chlorophenyl, 2-chloro-p-tolyl, (3-, 4-, 5-, or 6-)chloro-p-tolyl, 4-chloro-2-propylphenyl, 2-isopropyl-4-chlorophenyl, 4-chloro-3,5-xylyl, (2,3- 2,4-, 2,5-, 2,6-, 3,4-, or 3,5-)dichlorophenyl, 4-chloro-3-fluorophenyl, (3- or 4-)chloro-2-fluorophenyl, o-, m-, or p-trifluoromethylphenyl, (o-, m-, or p-methoxyphenyl, (o-, m-, or p-)ethoxyphenyl, 4- or 5-)chloro-2-methoxyphenyl, and 2,4-dichloro(5- or 6-)methylphenyl.

The novel prostaglandin analogs of this invention correspond to the prostaglandins described above in that the novel prostaglandin analogs exhibit prostaglandin-like activity.

Specifically the 9-deoxy-9-methylene-PGF-type compounds of this invention correspond to the PGE compounds described above, in that these novel 9-deoxy-9-methylene-PGF-type compounds are useful for each of the above-described purposes for which the PGE compounds are used, and are used in the same manner as the PGE compounds, as described above.

The PGE compounds described above, are all potent in causing multiple biological responses even at low doses. Moreover, for many applications, these prostaglandins have an inconveniently short duration of biological activity. In striking contrast, the novel prostaglandin analogs of this invention are substantially more selective with regard to potency in causing prostaglandin-like biological responses, and have a substantially longer duration of biological activity. Accordingly, each of these novel prostaglandin analogs is surprisingly and unexpectedly more useful than one of the corresponding prostaglandins described above for at least one of the pharmacological purposes indicated above for the latter, because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Another advantage of the novel prostaglandin analogs of this invention, especially the preferred PG analogs defined hereinbelow, compared with the corresponding prostaglandins, is that these novel pG analogs are administered effectively orally, sublingually, intravaginally, buccally, or rectally in those cases wherein the corresponding prostaglandin is effective only by the intravenous, intramuscular, or subcutaneous injection or infusion methods of administration indicated above as uses of these prostaglandins. These alternate routes of administration are advantageous because they facilitate maintaining uniform levels of these compounds in the body with fewer, shorter, or smaller doses and make possible self-administration by the patient.

Accordingly, the novel prostaglandin analogs of this invention are administered in various ways for obvious purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For intravenous injection or infusion, sterile aqueous isotonic solutions are preferred. For that purpose, it is preferred because of increased water solubility that $R_1$ in the novel compounds of this invention be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual adminstration. For rectal or vaginal administration, suppositories prepared as known in the art are used. For tissue implants, a sterile tablet or silicone rubber capsule or other object containing or impregnated with the substance is used.

The chemical structure of the novel 9-deoxy-9-methylene-PGF-type compounds of this invention renders them less sensitive to dehydration and rearrangement than the corresponding PGE compounds, and these novel compounds accordingly exhibit a surprising and unexpected stability and duration of shelf life.

When $X_1$ is —$COOR_1$, the novel PG analogs so described are used for the purposes described above in the free acid for, in ester form, in pharmacologically acceptable salt form. When the ester form is used, the ester is any of those within the above definition of $R_1$. However, it is preferred that the ester be alkyl of one to 12 atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel prostaglandin analogs of this invention compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediaine, diethylenetriamine, and the like aliphatic, cycloaliphatic, araaliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylgycamine, N-methylglucosamine, ephedrine, phenylephrine, epinephrine, procaine, and the like. Further useful amine salts are the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

The novel PG analogs of this invention are used for the purposes decribed above in free hydroxy form or also in the form wherein the hydroxy moieties are transformed to lower alkanoate moieties such as acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above decribed purposes are the acetoxy compounds. These free hydroxy and alkanoyloxy compounds are used as free acids, as esters, and in salt form all as described above.

To obtain the optimum combination of biological response specificity, potency, and duration of activity, certain compounds within the scope of this invention are preferred.

It is preferred that in the carboxy-terminated side chain be either one or 3, especially one, i.e., the natural chain length of the prostaglandins. Further when the other side chain contains —(CH$_2$)$_m$—CH$_3$, it is preferred that m be 3. For those compounds wherein R$_7$ is

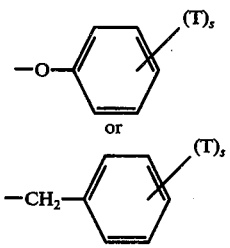

it is preferred that s be zero or one and T be chloro, fluoro, or trifluoromethyl.

For these compounds wherein at least one of R$_3$ and R$_4$ is methyl or fluoro, it is preferred that R$_5$ be hydrogen. For those compounds wherein R$_5$ is methyl, it is preferred that R$_3$ and R$_4$ both be hydrogen. For those compounds wherein R$_7$ is

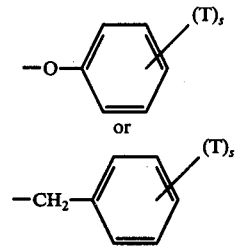

it is preferred that R$_3$, R$_4$, and R$_5$ all be hydrogen.

It is further preferred that the 15-hydroxy not be of the 15-epi configuration, i.e., that the hydroxy be in the alpha configuration.

Especially preferred are those compounds which satisfy two or more of the above preferences. Further, the above preferences are expressly intended to describe the preferred compounds within the scope of any generic formula of novel prostaglandin analogs disclosed herein. Thus, for example the above preferences describe preferred compounds within the scope of each formula of a prostaglandin analog provided in the Tables hereinafter.

The Charts herein describe methods whereby the novel prostaglandin analogs of this invention are prepared.

With respect to the Charts L$_1$, L$_2$, L$_3$, M$_1$, R$_1$, R$_5$, R$_7$, Z$_1$, g, m, and Y$_1$ are as defined above;

M$_4$ is

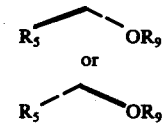

wherein R$_5$ is as defined above and R$_9$ is an acyl protecting group. M$_5$ is

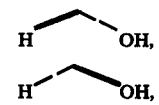

or a mixture of

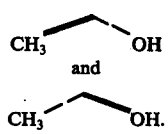

M$_6$ is

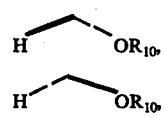

or a mixture of

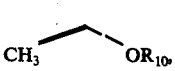

-continued
and

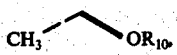

wherein $R_{10}$ is a blocking group.
$M_{19}$ is

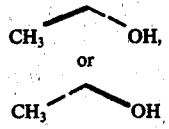

when $R_5$ is methyl, and

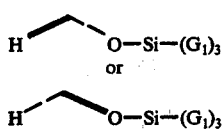

when $R_5$ is hydrogen, wherein $G_1$ is as defined below.

$R_2$ is hydrogen or fluoro. $R_8$ is hydrogen or hydroxy, $R_{16}$ is hydrogen or $-OR_9$, wherein $R_9$ is an acyl protecting group as defined below. $R_{18}$ is hydrogen or $-OR_{10}$, wherein $R_{10}$ is as defined above. $R_{26}$ is hydrocarbyl, including alkyl, aralkyl, cycloalkyl, and the like. Examples of these hydrocarbyl groups include 2-methylbutyl, isopentyl, heptyl, octyl, nonyl, tridecyl, octadecyl, benzyl, phenethyl, p-methylphenethyl, 1-methyl-3-phenylpropyl, cyclohexyl, phenyl, and p-methylphenyl.

$R_{38}$ is hydrogen or $-O-Si-(G_1)_3$.

$G_1$ is alkyl of one to 4 carbon atoms, cycloalkyl of 3 to 10 carbon atoms, inclusive, aralkyl of 7 to 12 carbon atoms, phenyl, or phenyl substituted with one or 2 fluoro, chloro, or alkyl of one to 4 carbon atoms, with the proviso that in the $-Si-(G_1)_3$ moiety the various $G_1$'s are the same or different.

$R_9$ is an acyl protecting group. Acyl protecting groups according to $R_9$, include:

a. Benzoyl;
b. Benzoyl substituted with one to 5, inclusive, alkyl of one to 4 carbon atoms, inclusive, phenylalkyl of 7 to 12 carbon atoms, inclusive, or nitro, with the proviso that not more than 2 substituents are other than alkyl, and that the total number of carbon atoms in the substituents does not exceed 10 carbon atoms, with the further proviso that the substituents are the same or different;
c. Benzoyl substituted with alkoxycarbonyl of 2 to 5 carbon atoms, inclusive;
d. Naphthoyl;
e. Naphthoyl substituted with one to 9, inclusive, alkyl of one to 4 carbon atoms, inclusive, phenylalkyl of 7 to 10 carbon atoms, inclusive, or nitro, with the proviso that not more than 2 substituents on either of the fused aromatic rings are other than alkyl and that the total number of carbon atoms in the substituents on either of the fused aromatic rings does not exceed 10 carbon atoms, with the further proviso that the various substituents are the same or different; or
f. Alkanoyl of 2 to 12 carbon atoms, inclusive.

In preparing these acyl derivatives of a hydroxy-containing compound herein, methods generally known in the art are employed. Thus, for example, an aromatic acid of the formula $R_9OH$, wherein $R_9$ is as defined above (e.g., benzoic acid), is reacted with the hydroxy-containing compound in the presence of a dehydrating agent, e.g. sulfuric acid, zinc chloride, or phosphoryl chloride; or alternatively an anhydride of the aromatic acid of the formula $(R_9)_2O$ (e.g., benzoic anhydride) is used.

Preferably, however, the process described in the above paragraph proceeds by use of the appropriate acyl halide, e.g., $R_9Hal$, wherein Hal is chloro, bromo, or iodo. For example, benzoyl chloride is reacted with the hydroxy-containing compound in the presence of a hydrogen chloride scavenger, e.g. an amine such as pyridine, triethylamine or the like. The reaction is carried out under a variety of conditions, using procedures generally known in the art. Generally mild conditions are employed: 20°-60° C., contacting the reactants in a liquid medium (e.g., excess pyridine or an inert solvent such as benzene. toluene, or chloroform). The acylating agent is used either in stoichiometric amount or in substantial stoichiometric excess.

As examples of $R_9$, the following compounds are available as acids ($R_9OH$), anhydrides (($R_9)_2O$), or acyl chlorides ($R_9Cl$): benzoyl; substituted benzoyl, e.g., 2-, 3-, or 4-)-methylbenzoyl, (2-, 3-, or 4-)-ethyl benzoyl, (2-, 3-, or 4-)-isopropylbenzoyl, (2-, 3-, or 4-)-tert-butylbenzoyl, 2,4-dimethylbenzoyl, 3,5-dimethylbenzoyl, 2-isopropyltoluyl, 2,4,6-trimethylbenzoyl, pentamethylbenzoyl, alphaphenyl-(2-, 3-, or 4-)-toluyl, (2-, 3-, or 4-)-phenethylbenzoyl, (2-, 3-, or 4-)-nitrobenzoyl, (2,4-, 2,5-, or 2,3-)-dinitrobenzoyl, 2,3-dimethyl-2-nitrobenzoyl, 4,5-dimethyl-2-nitrobenzoyl, 2-nitro-6-phenethylbenzoyl, 3-nitro-2-phenethylbenzoyl, 2-nitro-6-phenethylbenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)-methyl-1-naphthoyl, (2- or 4-) ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)-nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl.

There may be employed, therefore, benzoyl chloride, 4-nitrobenzoyl chloride, 3,5-dinitrobenzoyl chloride, or the like, i.e. $R_9Cl$ compounds corresponding to the above $R_9$ groups. If the acyl chloride is not available, it is prepared from the corresponding acid and phosphorus pentachloride as is known in the art. It is preferred that the $R_9OH$, $(R_9)_2O$, or $R_9Cl$ reactant does not have bulky hindering substituents, e.g. tert-butyl on both of the ring carbon atoms adjacent to the carbonyl attaching cite.

The acyl protecting groups, according to $R_9$, are removed by deacylation. Alkali metal carbonates are employed effectively at ambient temperature for this purpose. For example, potassium carbonate in methanol at about 25° C. is advantageously employed.

Those blocking groups within the scope of $R_{10}$ are any group which replaces a hydroxy hydrogen and is neither attacked nor reactive to the reagents used in the transformations used herein as an hydroxy is and which is subsequently replaceable with hydrogen in the preparation of the prostaglandin-type compounds. Several blocking groups are known in the art, e.g. tetrahydropyranyl and substituted tetrahydropyranyl. See for reference E. J. Corey, Proceedings of the Robert A. Welch Foundation Conferences on Chemical Research, 12, Organic Synthesis, pgs. 51–79 (1969). Those blocking groups which have been found useful include
a. tetrahydropyranyl;
b. tetrahydrofuranyl; and
c. a group of the formula $$-C(OR_{11})\ (R_{12})-CH(R_{13})(R_{14}),$$

wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together $-(CH_2)_a-$ or $-(CH_2)_b-O-(CH_2)_c$, wherein a is 3, 4, or 5, or b is one, 2, or 3, and c is one, 2, or 3, with the proviso that b plus c is 2, 3, or 4, with the further proviso that $R_{12}$ and $R_{13}$ may be the same or different, and wherein $R_{14}$ is hydrogen or phenyl.

When the blocking group $R_{10}$ is tetrahydropyranyl, the tetrahydropyranyl ether derivative of any hydroxy moieties of the PG-type intermediates herein is obtained by reaction of the hydroxy-containing compound with 2,3-dihydropyran in an inert solvent, e.g. dichloromethane, in the presence of an acid condensing agent such as p-toluenesulfonic acid or pyridine hydrochloride. The dihydropyran is used in large stoichiometric excess, preferably 4 to 10 times the stoichiometric amount. The reaction is normally complete in less than an hour at 20° to 50° C.

When the blocking group is tetrahydrofuranyl, 2,3-dihydrofuran is used, as described in the preceding paragraph, in place of the 2,3-dihydropyran.

When the blocking group is of the formula $$-C(OR_{11})\ (R_{12})-CH(R_{13})\ (R_{14}),$$

wherein $R_{11}$, $R_{12}$, $R_{13}$, and $R_{14}$ are as defined above, the appropriate reagent is a vinyl ether, e.g. isobutyl vinyl ether or any vinyl ether of the formula $$C(OR_{11})\ (R_{12})=C(R_{13})\ (R_{14}),$$

wherein $R_{11}$, $R_{12}$, $R_{13}$, and $R_{14}$ are as defined above; or an unsaturated cyclic or heterocyclic compound, e.g. 1-cyclohexen-1-yl methyl ether, or 5,6-dihydro-4-methoxy-2H-pyran. See C. B. Reese, et al., Journal of the Chemical Society 89, 3366 (1967). The reaction conditions for such vinyl ethers and unsaturated compounds are similar to those for dihydropyran above.

The blocking groups according to $R_{10}$ are removed by mild acidic hydrolysis. For example, by reaction with (1) hydrochloric acid in methanol; (2) a mixture of acetic acid, water, and tetrahydrofuran; or (3) aqueous citric acid or aqueous phosphoric acid in tetrahydrofuran, at temperatures below 55° C., hydrolysis of the blocking groups is achieved.

The symbol "n" is one or 2.

$Y_2$ is trans—$CH=C(Hal)$—, wherein Hal is chloro, bromo, or iodo, —$CH_2CH_2$—, or trans—$CH=CH$—.

$Z_2$ is cis—$CH=CH-CH_2-(CH_2)_g$—

Chart A

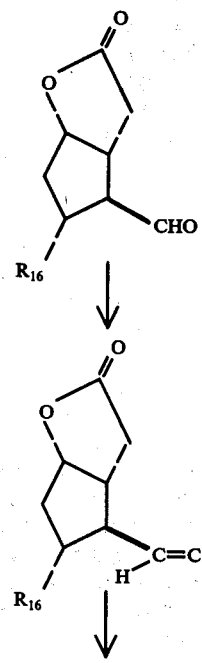

XXI

XXII

-continued
Chart A
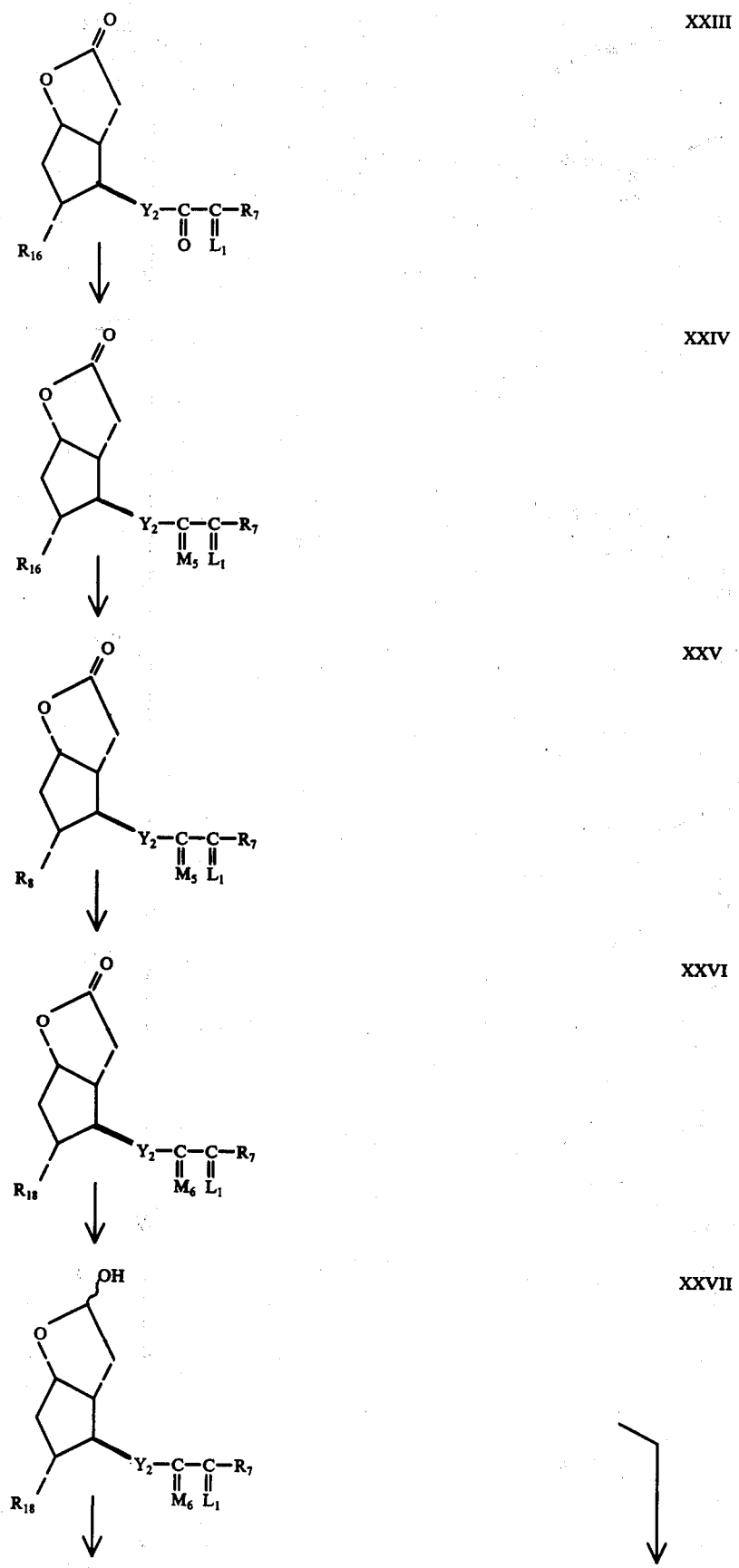

-continued
Chart A
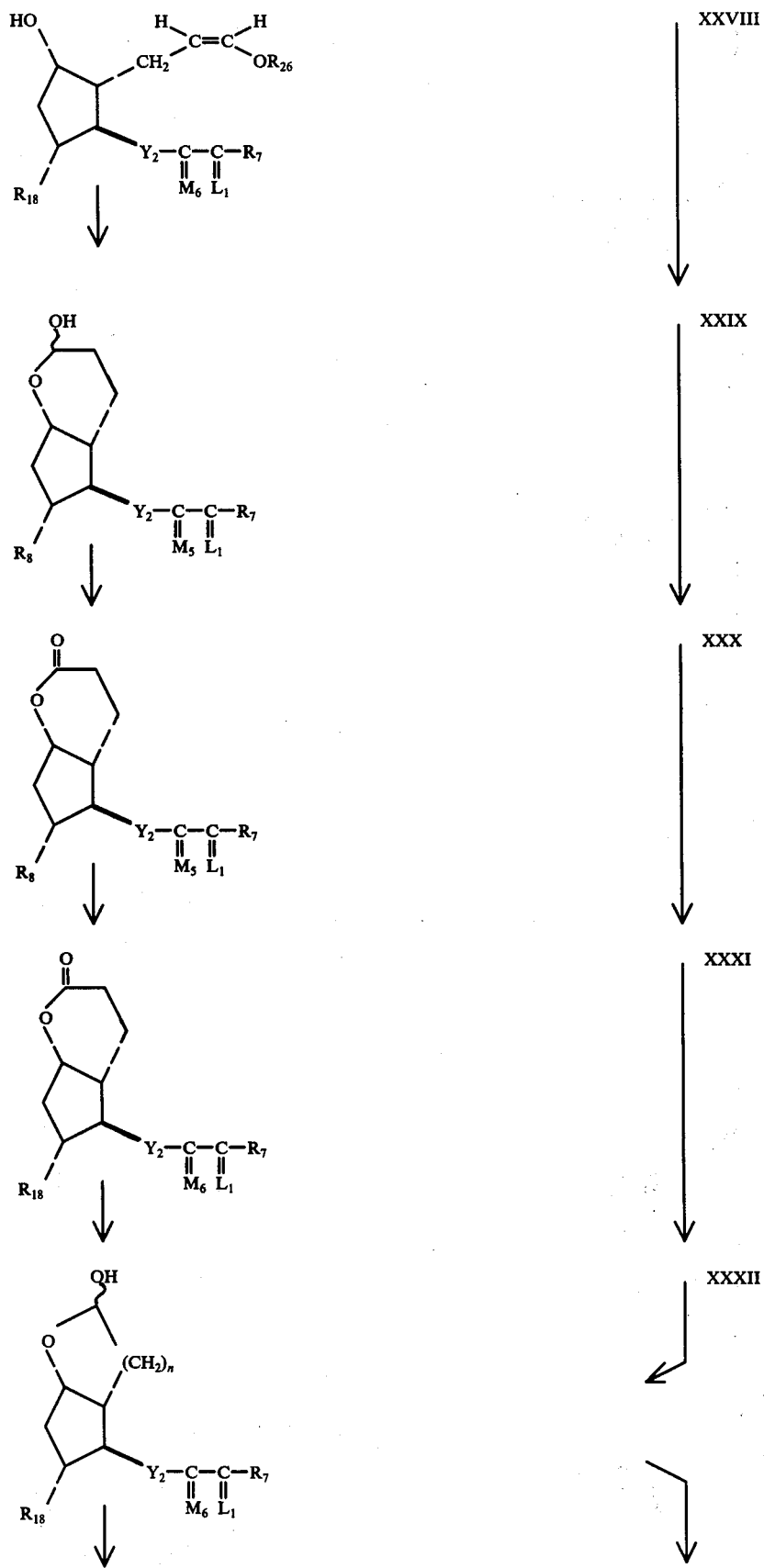
XXVIII
XXIX
XXX
XXXI
XXXII

-continued
Chart A
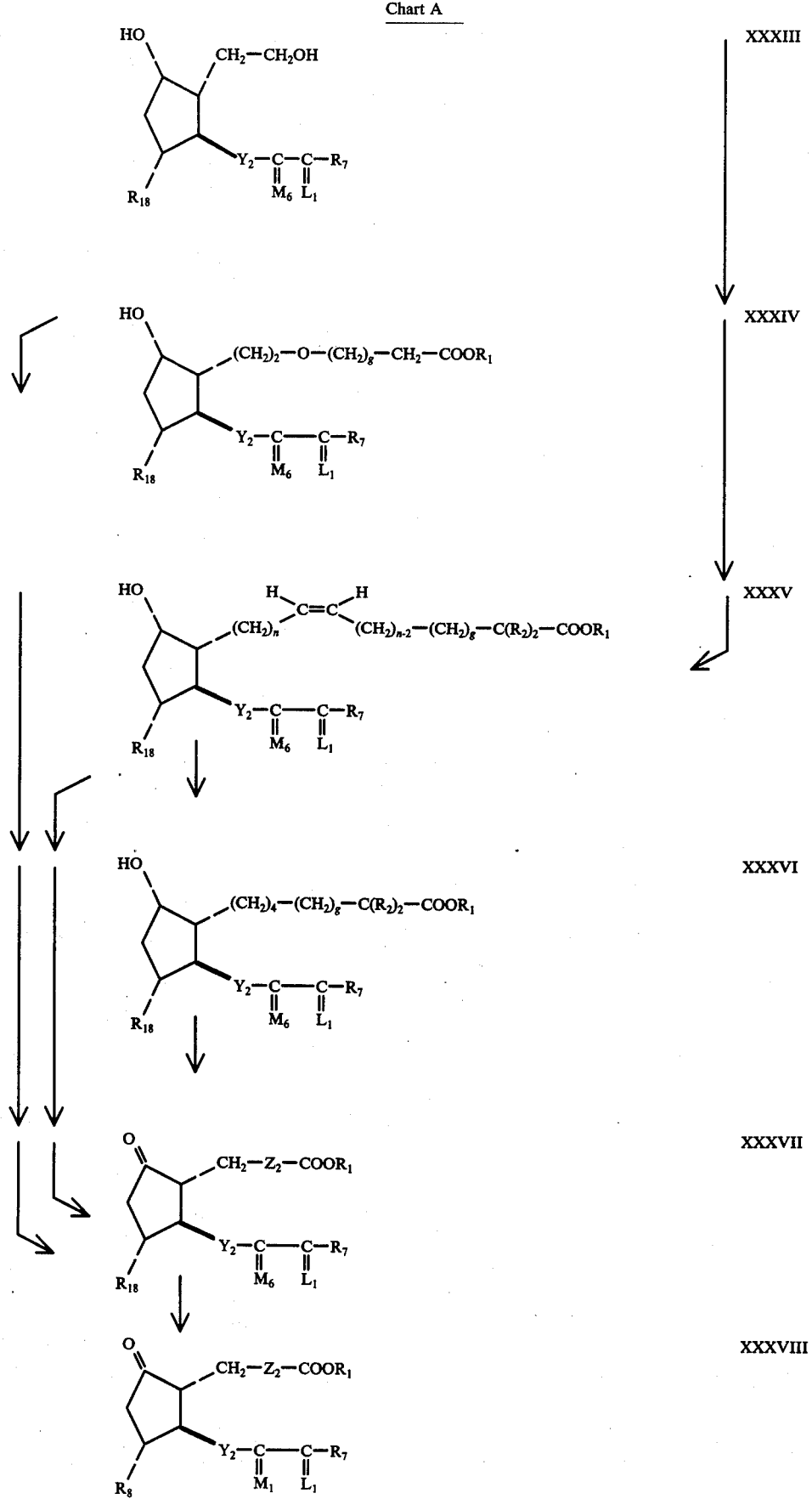
XXXIII
XXXIV
XXXV
XXXVI
XXXVII
XXXVIII

Chart B
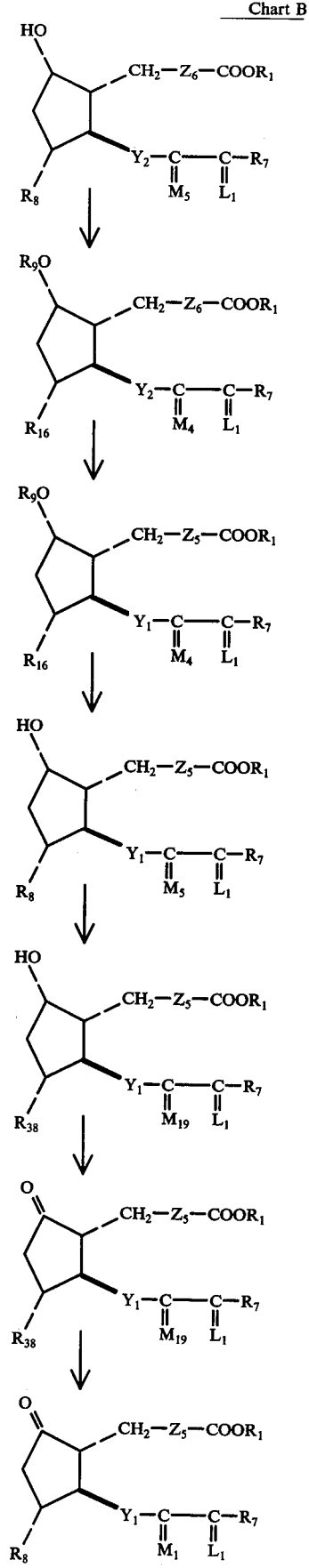
Chart C
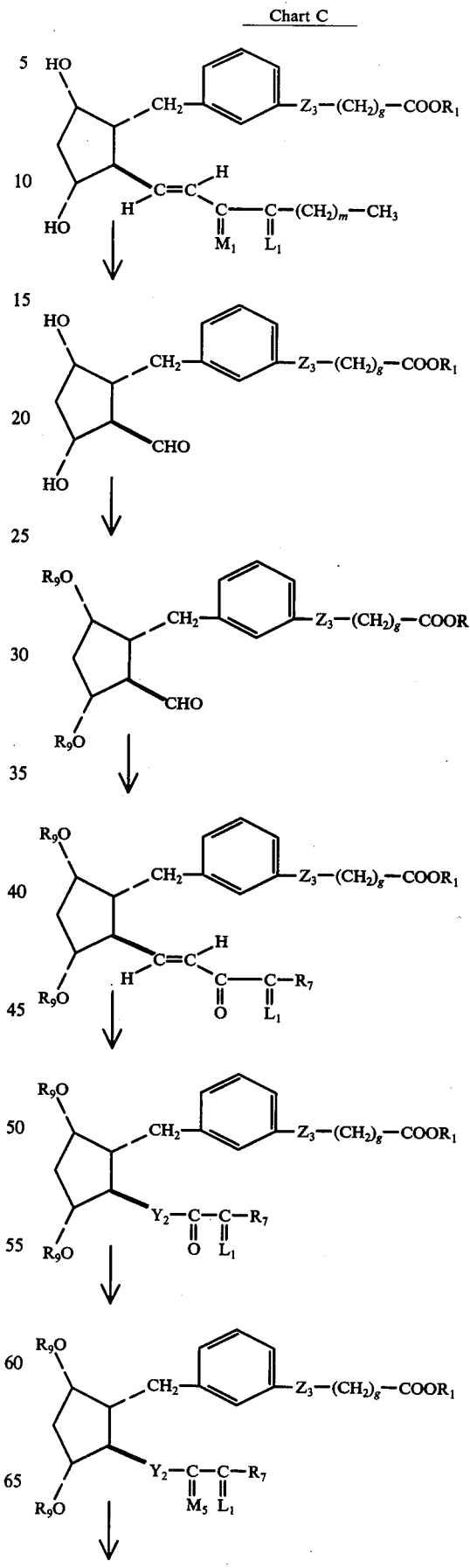

-continued
LVII
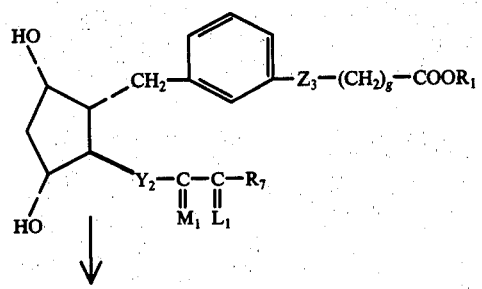
LVIII
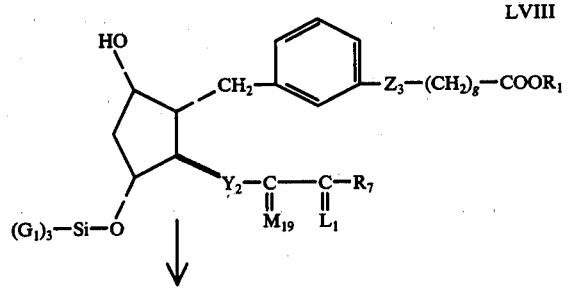
LIX
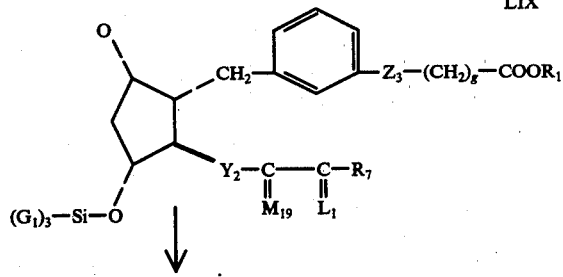
LX
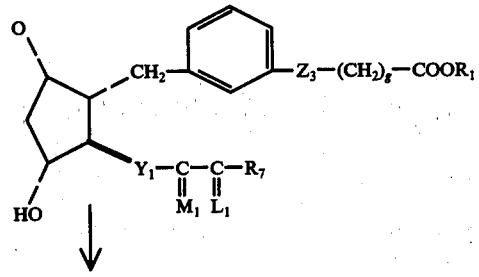
LXI
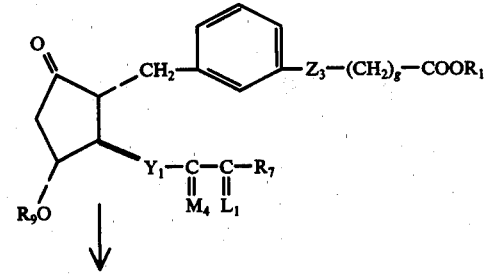
LXII
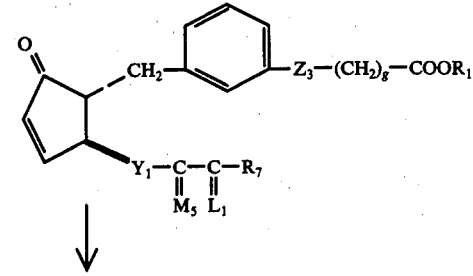
-continued
LXIII
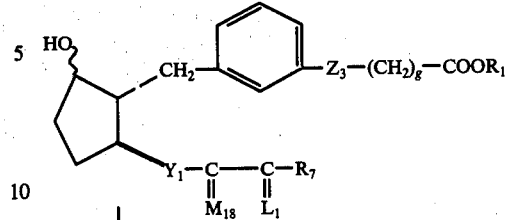
LXIV
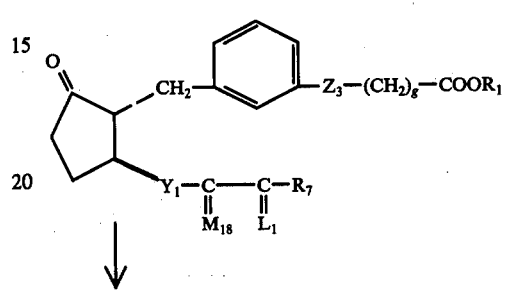
LXV
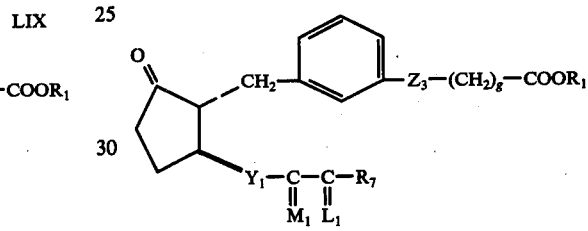
Chart D
LXXI
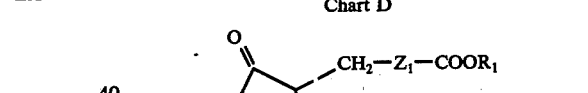
LXXII
LXXIII
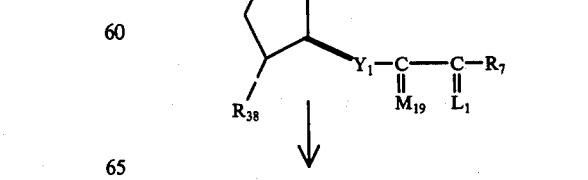

-continued
LXXIV 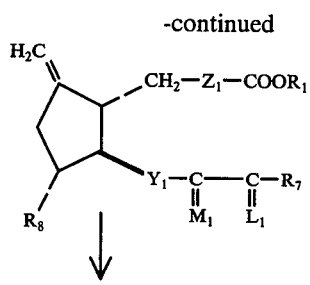
Chart E
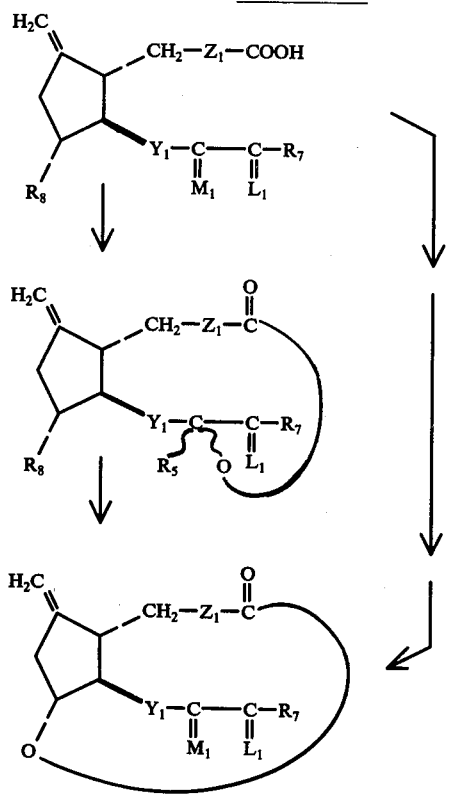
Chart F
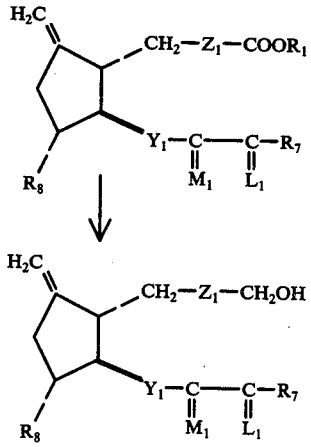
Chart G
-continued
CI 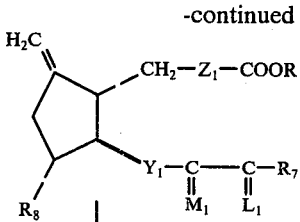
CII 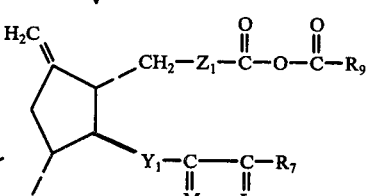
CIII 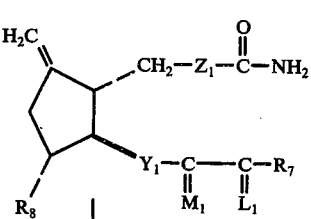
CIV 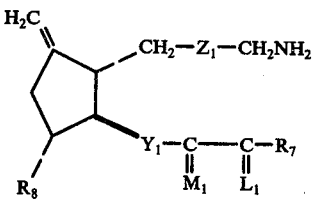
CV 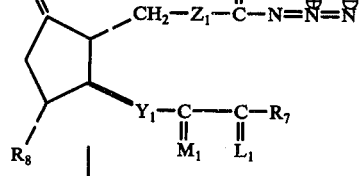
CVI 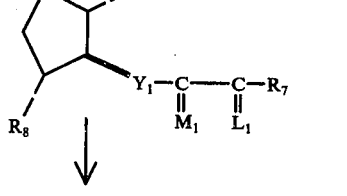
CVII 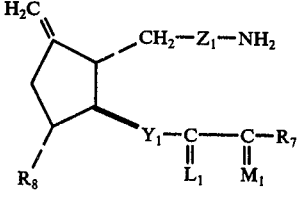

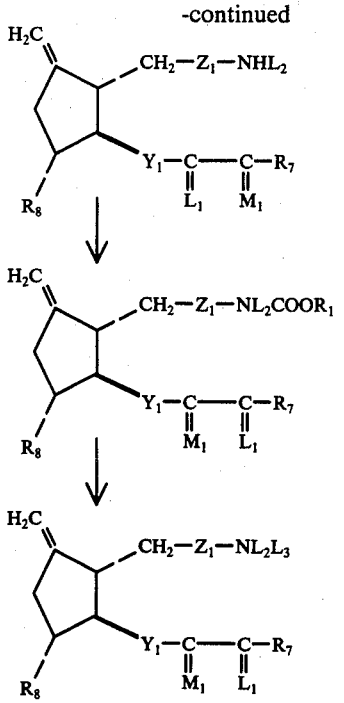

$C(R_2)_2$—, cis—$CH_2$—CH=CH—$(CH_2)_g$—$CH_2$, —$(CH_2)_3$—$(CH_2)_g$—$(R_2)_2$—, or —$CH_2$—O—$CH_2$—$(CH_2)_g$—$CH_2$—, wherein $R_2$ and g are as defined above. $Z_3$ is oxa or methylene. $Z_5$ is —C≡C—$CH_2$—$(CH_2)_g$—$CH_2$—or —$CH_2$—C≡C—$(CH_2)_g$—$CH_2$—, $Z_6$ is cis—CH=CH—$CH_2$—$(CH_2)_g$—$CH_2$—or cis- —$CH_2$—CH=CH—$(CH_2)_g$—$CH_2$—.

Charts A-C herein provide methods whereby starting materials useful for preparing the novel prostaglandin analogs of the present invention according to Charts D-G are prepared.

With respect to Chart A a method is provided whereby the formula XXI bicyclic lactone aldehyde, known in the art in either optically active or racemic form, is transformed to the formula XXXIVIII PGE- or 11-deoxy-PGE-type compounds. The various reaction steps of Chart A are known in the art.

The formula XXII compound is prepared from the formula XXI compound by a Wittig alkylation. Reagents known in the art or prepared by methods known in the art are employed. The transenone lactone is obtained stereospecifically. See for reference D. H. Wadsworth, et al., Journal of Organic Chemistry 30, 680 (1965).

In the preparation of the formual XXII compound, certain phosphonates are employed in the Wittig reaction. These phosphonates are of the general formula

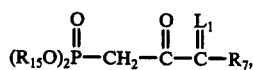

wherein $L_i$ and $R_7$ are as defined above and $R_{15}$ is alkyl of one to 8 carbon atoms, inclusive.

Phosphonates of the above general formula are prepared by methods known in the art. See Wadsworth, et al. as cited above.

Conveniently the appropriate aliphatic acid ester is condensed with the anion of dimethyl methylphosphonate as produced using n-butyllithium. For this purpose, acids of the general formula

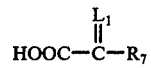

are employed in the form of their lower alkyl esters, preferably methyl or ethyl. The methyl esters for example are readily obtained by reaction of the corresponding acids with diazomethane.

For example, when $R_7$ is

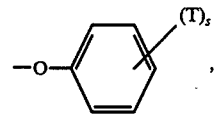

wherein T and s are as defined above, and $R_3$ and $R_4$ of the $L_1$ moiety are both hydrogen, the corresponding phenoxy or substituted phenoxy acetic acids are known in the art or readily available in the art. Those known in the art include those wherein the $R_7$ moiety is: phenoxy, (o-, m-, or p-)tolyloxy-, (o-, m-, or p-)ethylphenoxy-, 4-ethyl-o-tolyloxy-, (o-, m-, or p-)propylphenoxy-, (o-, m-, or p-)-t-butylphenoxy-, (o-, m-, or p-)fluorophenoxy-, 4-fluoro-2,5-xylyloxy-, (o-, m-, or p-)chlorophenoxy-, (2,3-, 2,4-, 2,5-, 2,6-, 3,4-, or 3,5-)dichlorophenoxy-, (o-, m-, or p-)trifluoromethylphenoxy-, or (o-, m-, or p-)methoxyphenoxy-.

Further, many 2-phenoxy- or substituted phenoxy propionic acids are readily available, and are accordingly useful for the preparation of the acids of the above formula wherein one and only one of $R_3$ and $R_4$ of the $L_1$ moiety is methyl and $R_7$ is phenoxy or substituted phenoxy. These 2-phenoxy or 2-substituted phenoxy propionic acids include those wherein the $R_7$ moiety is p-fluorophenoxy-, (o-, m-, or p-)chlorophenoxy-, (2,3-, 2,4-, 2,5-, 2,6-, 3,4-, or 3,5-)dichorophenoxy-, (4- or 6-chloro-o-tolyloxy-, phenoxy-, (o-, m-, or p-)tolyloxy, 3,5-xylyloxy-, or m-trifluoromethylphenoxy-.

Finally there are available many 2-methyl-2-phenoxy- or (2-substituted)phenoxypropionic acids, which are useful in the preparation of the above acids wherein $R_3$ and $R_4$ of the $L_1$ moiety are both methyl and $R_7$ is phenoxy or substituted phenoxy. These 2-methyl-2-phenoxy-, or (2-substituted)phenoxypropionic acids include those wherein $R_7$ is: phenoxy-, (o-, m-, or p-)chlorophenoxy-, (2,3-, 2,4-, 2,5, 2,6-, 3,4-, or 3,5-)dichlorophenoxy-.

Other phenoxy substituted acids are readily available by methods known in the art, for example, by Williamson synthesis of ethers using an α-halo aliphatic acid or ester with sodium phenoxide or a substituted sodium phenoxide. Thus, the (T)$_s$-substituted sodium phenoxide is reacted with, for example, the α-chloro aliphatic acid, or the alkyl ester derivative thereof, with heating to yield the acid of the above general formula, which is recovered from the reaction mixture by conventional purification techniques.

There are further available phenyl substituted acids of the above formula wherein $R_7$ is benzyl or substituted benzyl.

For example, when $R_3$ and $R_4$ of the $L_1$ moiety are both hydrogen there are available the following phenyl or substituted propionic acids: (o-, m-, or p-)-chlorophenyl-, p-fluorophenyl-, m-trifluoromethylphenyl-, (o-, m-, or p-)methylphenyl-, (o-, m-, or p-)methoxyphenyl-, (2,4-, 2,5-, or 3,4-)dichlorophenyl-,.(2,3-, 2,4-, 2,5-, 2,6-, or 3,4-)dimethylphenyl-, or (2,3-, 2,4-, 2,5-, 2,6-, 3,4-, or 3,5-)dimethoxyphenyl-.

When one and only one of $R_3$ and $R_4$ of the $L_1$ moiety is methyl there are available, for example, the following 2-methyl-3-phenyl or substituted phenyl propionic acids: phenyl, o-chlorophenyl-, o-, or p-)methylphenyl-, (o-, m-, or p-)methoxyphenyl-, (2,4- or 3,4-)difluorophenyl-, 2,3-dimethylphenyl-, and (2,3-, 3,4-, or 4,5-)dimethoxyphenyl-.

When both $R_3$ and $R_4$ are methyl there are available, for example, the following 2,2-dimethyl-3-phenyl or substituted phenyl propionic acids: phenyl- and p-methylphenyl.

When one and only one $R_3$ and $R_4$ is fluoro, there is available, for example, 2-fluoro-3-phenyl propionic acid.

Phenyl substituted acids (as above wherein $R_7$ is benzyl) are available by methods known in the art, for example, by reacting a mixture of the appropriate methyl- or fluoro-substituted acetic acid, a secondary amine (e.g., diisopropylamine), n-butyllithium, and an organic diluent (e.g., tetrahydrofuran with the appropriately substituted benzyl chloride. Thus, the above acid is obtained by the following reaction:

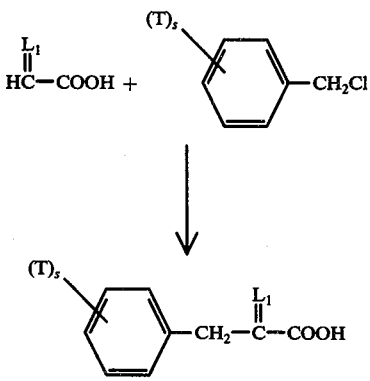

The above reaction proceeds smoothly, ordinarily at 0° C. The product acid is recovered using conventional methods.

For the acids of the above formula wherein $R_7$ is n-alkyl, many such acids are readily available.

For example, when $R_3$ and $R_4$ of the $L_1$ moiety are both hydrogen there are available butyric, pentanoic, hexanoic, heptaoic, and octanoic acids.

For example, when one and only one of $R_3$ and $R_4$ of the $L_1$ moiety is methyl, there are available the following 2-methyl alkanoic acids: butyric, pentanoic, hexanoic, heptanoic, and octanoic.

For example, when one of $R_3$ and $R_4$ of the $L_1$ moiety is fluoro there are available the following 2-fluoro alkanoic acids: butyric, pentanoic, hexanoic, heptanoic, and octanoic.

The acids of the above general formula wherein $R_7$ is alkyl and $R_3$ and $R_4$ of the $L_1$ moiety are fluoro are conveniently prepared from the corresponding 2-oxoalkanoic acids, i.e. butyric, pentanoic, hexanoic, heptanoic, and octanoic. The transformation of these 2-oxoalkanoic acids to the corresponding 2,2-difluoro alkanoic acids proceeds by methods known in the art, using known ketonic fluorinating reagents. For example, $MoF_6 \cdot BF_3$ is advantageously employed in the fluorination. See Mathey, et al., Tetrahedron Lett. 27, 2965 (1971).

The formula XXIII compound wherein $Y_2$ is trans—CH=C(Hal)— is prepared from the formula XXII compound by dihalogenation, followed by dehydrohalogenation. The halogenation proceeds by methods known in the art, conveniently by reaction of the formula XXII compound with a reagent such as N-halosuccinimide. The reaction proceeds slowly to completion, ordinarily within three to ten days. Alternatively the molecular form of the halide $(Hal)_2$ in a diluent (e.g., carbon tetrachloride or a mixture of acetic acid and sodium acetate) is employed in this dihalogenation. Thereafter dehydrohalogenation proceeds by addition of an organic base, preferably amine base, to the halide. For example pyridine, or a diazobicycloalkene, is an especially useful amine base, although non-amine bases such as methanolic sodium acetate are likewise employed.

Optionally the formula XXIII compound wherein $Y_2$ is —CH=C(Hal)— is prepared directly from the formula XXI compound using A Wittig reagent derived from a 1-halophosphonate corresponding to the phosphonate described above for the preparation of the formula XXII compound. These phosphonates are known in the art or are readily prepared by methods known in the art. For example, a phosphonate as described above is transformed to the corresponding 1-halophosphonate by dripping the molecular halogen into a solution of the phosphonate and a strong organic base, e.g. sodium methoxide.

The 1-halophosphate are prepared above is then reacted with the formula XXI compound in a manner described for the preparation of the formula XXII compound from the formula XXI compound to prepare the formula XXIII compound.

In any event, the 14-chloro rather than 14-bromo or 14-iodo intermediates are preferred formula XXIII products, in that they lead to PG intermediates which are more easily dehydrohalogenated at C-13 and C-14 according to the procedures hereinafter described.

In each of the above described methods for the preparation of the formula XXIII compound wherein $Y_2$ is trans-CH=C(Hal)- the desired formula XXIII product is often contaminated with its corresponding cis isomer. In performing the below steps it is particularly desirable to obtain pure formula XXIII product in order to avoid creation of complicated mixtures of stereoisomers. Accordingly, the formula XXIII compound is subjected to conventional separation techniques (e.g. silica gel chromatography) to obtain pure product.

The formula XXIII compound wherein $Y_2$ is —$CH_2CH_2$— is prepared from the formula XXII compound by catalytic hydrogenation, employing methods known in the art.

The formula XXIV compoud is prepared from the formula XXIII 3-oxo bicyclic lactone by transformation of the 3-oxo-moiety to the $M_5$ moiety.

The above 3-oxo bicyclic lactone is transformed to the ester, a 3α or 3β-hydroxy bicyclic lactone, wherein $M_5$ is

by reduction of the 3-oxo moeity, followed by separation of the 3α- and 3β-hydroxy epimers. For this reduction the known ketonic carbonyl reducing agents which do not reduce ester or acid groups or carbon-carbon double bonds (when such reduction is udesirable) are employed. Examples of these agents are the metal borohydrides, especially sodium, potassium, and zinc borohydrides, lithium(tri-tert-butoxy)-aluminum hydride, metal trialkyl borohydrides, e.g. sodium trimethoxy borohydride, lithium borohydride, and the like. In those cases in which carbon-carbon double bonds are not present the boranes, e.g. disiamylborane (bis-3-methyl-2-butyl borane) are alternatively employed.

For the production of C-15 epimerically pure prostaglandins, the 15-epi compound is separated from the mixture by methods known in the art. For example, silica gel chromatography is advantageously employed.

The 3-oxo bicyclic lactone is transformed into the corresponding (3RS)-3-methyl bicyclic lactone wherein $M_5$ is a mixture of

by reaction of the 3-oxo bicyclic lactone with a Grignard reagent, $CH_3MgHal$, wherein Hal is chloro, bromo, or iodo. The Grignard complex is thereafter hydrolyzed, for example, using saturated aqueous ammonium chloride as is known in the art. An alternate method for transforming the 3-oxo compound to a 3(RS)-3-methyl compound is by reaction of the 3-oxo bicyclic lactone with trimethylaluminum.

The preferred method for separation of these (3RS)-3-methyl epimers is by separation of the corresponding C-15 epimers of the PG-type, methyl esters using silica gel chromatography or high pressure liquid chromatography (HPLC). The formula XXV compound is prepared from the formula XXIV compound by deacylation, as described above. The formula XXVI compound is then prepared from the formula XXV compound by replacing any free hydroxy moieties with blocking groups according to $R_{10}$ by the procedure described above. The formula XXVII compound is then prepared from the formula XXVI compound by reduction of the formula XXVI lactone to a lactol. Methods known in the art are employed. For example, diisobutylaluminum hydride is employed at $-60°$ to $-70°$ C.

The formula XXVII compound undergoes condensation to form the formula XXVIII enol ether. For this purpose a hydrocarbyloxy, and preferably an alkoxymethylenetriphenylphosphorane is useful. See for reference, Levine, Journal of the American Chemical Society 80, 6150 (1958). The reagent is conveniently prepared from a corresponding quaternary phosphonium halide in a base, e.g. butyllithium or phenyllithium, at low temperature, e.g. preferably below $-10°$ C. The formula XXVII lactol is mixed with the above reagent and the condensation proceeds smoothly within the temperature range of $-30° - +30°$ C. At higher temperatures the reagent is unstable, whereas at low temperatures the rate of condensation is undesirably slow. Examples of alkoxymethylenetriphenylphosphoranes preferred for the above purposes are methoxy-, ethoxy-, propoxy-, isopropoxy-, butoxy-, isobutoxy-, s-butyoxy-, and t-butoxy-methylenetriphenylphosphorane. Various hydrocarbyloxymethylenetriphenylphosphoranes which are optionally substituted for the alkoxymethylenetriphenylphosphoranes are accordingly useful for preparing the formula XXVII intermediates wherein $R_{26}$ is hydrocarbyl, include alkoxy-, aralkoxy-, cycloalkoxy-, and aryloxymethylenetriphenylphosphoranes. Examples of these hydrocarbyloxytriphenylphosphoranes are 2-methyl butyloxy-, isopentyloxy-, heptyloxy-, octyloxy-, nonyloxy-, tridecyloxy-, octadecyloxy-, benzyloxy-, phenethyloxy-, p-methylphenethyloxy-, 1-methyl-3-phenylpropyloxy-, cyclohexyloxy-, phenoxy-, and p-methylphenoxy-, phenoxymethylenetriphenylphosphorane. See for reference, Organic Reactions, Vol. 14, pg. 346–348, John Wiley and Sons, New York, New York, (1965). The formula XXVIII enol intermediates are then hydrolyzed to the formula XXIX lactols. This hydrolysis is done under acidic conditions for example with perchloric acid or acetic acid. Tetrahydrofuran is a suitable diluent for this reaction mixture. Reaction temperatures of from 10° to 100° C. are employed. The length of time required for hydrolysis is determined in part by the hydrolysis temperature and using acetic acid-water-tetrahydrofuran at about 60° C. several hr. are sufficient to accomplish the hydrolysis.

The formula XXX compound is then prepared from the formula XXIX compound by oxidation of the formula XXIX lactol to a lactone. This transformation is carried out, using for example, silver oxide as an oxidizing reagent, and is followed by treatment with pyridine hydrochloride. Preparation of the formula XXXI compound proceeds from the formula XXX compound by transformation of any free hydroxy moieties to blocking groups according to $R_{10}$, following the procedures herein described for such a transformation.

Thereafter the formula XXXII compound (wherein n is 2) is prepared from the formula XXXI compound by reduction of the formula XXX lactone to a lactol. For example, diisobutylaluminum hydride is employed as is described above for the reduction of lactones to lactols. The formula XXXII lactol is alternately represented by the formula XXVII compound when n is one.

The formula XXXv compound is prepared from the formula XXXII compound by a Wittig alkylation, using the appropriate (ω-carboxyalkyl)triphenylphosphonium bromide. The reaction proceeds as is generally known in the art, by first mixing the appropriate (ω-carboxyalkyl)triphenylphosphonium bromide with sodio dimethyl sulfinylcarbanide, at ambient temperature, and adding the formula XXXII lactol to this mixture. Thereafter the carboxy hydrogen of the compound so formed is transformed to an $R_1$ moiety by the methods and procedures hereinbelow described. Accordingly, there is prepared the formula XXXV cis-4,5-didehydro-11-deoxy-PGF$_{1\alpha}$-, 11-deoxy-PGF$_{2\alpha}$-, cis-4,5-didehydro-PGF$_{1\alpha}$-, or PGF$_{2\alpha}$-type compound.

The formula XXXVI compound is then prepared from the formula XXXV compound by catalytic hydrogenation of the formula XXXV compound. Methods known in the art for transformation of PG$_2$-type compounds to PG$_1$-type compounds are employed. Accordingly, metal catalysts (e.g. palladium) on a suitable support (e.g. carbon) at about 0° C. are employed under a hydrogen atmosphere. See for reference B. Samuelsson, Journal of Biological Chemistry, 239, 491 (1974).

The formula XXXII lactol is transformed into the corresponding formula XXXIV 5-oxo-PGF$_{1\alpha}$-type intermediate first by reduction of the formula XXXII lactol, for example, with aqueous methanolic or ethanolic sodium borohydride to the formula XXXIII compound. Alternatively, and preferably, the formula XXXIII compound is obtained by a one step reduction of the formula XXXVI lactone, for example, with lithium aluminum hydride or diisobutyl aluminum hydride at a temperature ranging from 0° to 35° C. For preparing the formula XXXIV compound, a Williamson synthesis is employed. For example, the formula XXXIII compound is condensed with a haloalkanoate within the scope of

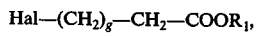

wherein Hal is chloro, bromo, or iodo and g is as defined above. Normally the reaction is done in the presence of a base such as n-butyllithium, phenyllithium, trimethyllithium, sodium hydride, or potassium t-butoxide.

Alternatively and preferably, an ortho-4-bromoalkanoate is employed. Such reagents are available or are prepared by methods known in the art, for example, from the appropriate halonitrile by way of the corresponding imino ester hydrohalide as illustrated hereinafter.

The condensation is conveniently run in a solvent, such as tetrahydrofuran or dimethyl sulfoxide or especially if an organolithium compound is employed, preferably in dimethylformamide or hexamethylphosphoramide. The reaction proceeds smoothly at −20° to 50° C., but is preferably performed at ambient temperature. Following the condensation, the formula XXXIV compound is obtained by methods known in the art, for example, by hydrolysis in cold dilute mineral acid.

Thereafter, the formula XXXVII compound is prepared from the formula XXXIV, XXXV, or XXXVI compound by oxidation of the 9-hydroxy to a 9-oxo. Oxidation methods known in the art for the transformation of PGF-type compounds to corresponding PGE-type compounds are employed. For example, the Jones reagent or the Collins reagent is advantageously used.

The formula XXXVIII compound is then prepared from the formula XXXVII compound or by first separating any mixed C-15 epimers, and thereafter hydrolyzing any blocking groups according to $R_{10}$. Acidic conditions are employed in the hydrolysis as is described above.

Certain (3RS)-3-methyl lactones of Chart A may be separated into their respective (3S)- or (3R)-epimers by silica gel chromatographic separation techniques. Where such separation is possible, this route is preferred. Accordingly, in these cases the separation is effected and $M_5$ is

and $M_6$ is

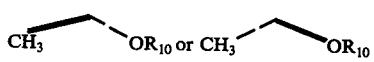

wherein $R_{10}$ is a blocking group. Accordingly, the separation procedure of PG-type intermediates is omitted when the optional lactone separation is employed.

Chart B provides a method whereby the formula XLI compound, prepared according to Chart A, is transformed to a formula XLVII 5,6-didehydro-PGE$_2$-, 5,6-didehydro-11-deoxy-PGE$_2$-, 4,4,5,5-tetradehydro-PGE$_1$-, or 4,4,5,5-tetradehydro-11-deoxy-PGE$_1$-type compound.

The formula XLII compound of Chart B is prepared from the formula XLI compound by replacing free hydroxy hydrogens with acyl protecting groups, according to $R_9$, following the procedure described above. Thereafter the formula XLII compound is transformed to the formula LXII 5,6-didehydro-PG$_2$-type compound or 4,4,5,5-tetradehydro-PG$_1$-type compound by halogenation (bromination or chlorination) followed by dehydrohalogenation.

The halogenation described above consists of transforming the formula XLII PGF$_{2\alpha}$- or 11-deoxy-PGF$_{2\alpha}$-type compound to a corresponding 5,6-dihalo-PG$_1$ or 11-deoxy-PG$_1$-type compound or transforming the formula XLII cis-4,5-didehydro-PGF$_{1\alpha}$- or 11-deoxy-PGF$_{1\alpha}$-type compound to a corresponding 4,5-dihalo-PGF$_{1\alpha}$- or 11-deoxy-PGF$_{1\alpha}$-type compound. This halogenation proceeds by mixture of the molecular halogen (e.g. BR$_2$ or Cl$_2$) with the formula XLII compound in a diluent which comprises a chlorinated hydrocarbon. Preferred reaction temperatures are between −40° and 0° C. with −20° C. being especially preferred. Chlorinated hydrocarbon intermediates preferred as diluents include carbon tetrachloride, chloroform, and dichloromethane. Thereafter, the formula XLIII compound is prepared by dehydrohalogenation with base. Amine bases are especially preferred, and in particular 1,5-diazobicyclo[5.4.0.]undecene-5 is preferred. See Fieser and Fieser, Vol. 2, page 101 (1969). Thereafter, the formula LXIV compound is prepared from the formula XLIII compound by deacylation, following procedures described hereinabove. Alternatively, dehydrohalogenation and deacylation are achieved in one step, employing potassium t-butoxide in dimethylsulfoxide.

When the above reactions hydrolyze an ester, the ester moiety is conveniently restored employing esterification methods described below.

Transformations XLIV to LXVII provide a method whereby the formula XLIV PGF$_\alpha$ or 11-deoxy-PGF$_\alpha$-type compound is transformed into the corresponding PGE- or 11-deoxy-PGE-type compound by selective silylation of all secondary hydroxy hydrogens of the formula XLIV compound, other than the C-9 hydroxy.

The formula LXV compound is prepared from the formula LXIV compound by selective silylation of the various secondary hydroxy groups of the formula XLIV compound over the C-9 rydroxy. Silyl groups with the scope -Si(G$_1$)$_3$, wherein G$_1$ is alkyl of one to 4 carbon atoms, inclusive, aralkyl of 7 to 12 carbon atoms, inclusive, phenyl, phenyl substituted with one or 2 chloro, fluoro, or alkyl of one to 4 carbon atoms, inclusive, with the proviso that the various G$_1$'s of the -Si(G$_1$)$_3$ moiety are the same or different, are employed. These reagents are known in the art and their use is known in the art.

For the selective silylation procedure methods known in the art for selective silylation of known prostanoic acid derivatives are employed. See for reference U.S. Pat. No. 3,822,303 (issued July 2, 1974), German Offenlegungsschrift 2,259,195 (Derwent Farmdoc CPI 36457U-B), and Netherlands Pat. No. 7,214,142 (Derwent Farmdoc CPI 26221U-B).

Examples of the -Si(G$_1$)$_3$ moiety are trimethylsilyl, dimethyl(tert-butyl)silyl and dimethylphenylsilyl. Examples of alkyl of one to 4 carbon atoms, inclusive, aralkyl of 7 to 12 carbon atoms, inclusive, and phenyl or substituted phenyl moieties are provided hereinabove.

The formula XLVI compound is prepared from the formula XLV compound by oxidation of the C-9 hydroxy to a C-9 oxo. Oxidation reagents and methods known in the art are employed. For example, the Jones or Collins Reagent is advantageously employed.

The formula XLVII compound is prepared from the formula XLVI compound by hydrolysis of the silyl groups. Hydrolysis proceeds by methods known in the art, e.g. the use of water or dilute aqueous acetic acid in a diluent of water and a quantity of a water miscible solvent sufficient to yield a homogeneous reaction mixture. This hydrolysis is ordinarily complete within 2 to 12 hr. at 25° C., and is preferably carried out in an atmosphere of an inert gas such as nitrogen or argon.

Chart C provides a method whereby the formula XLI 3,7-inter-m-phenylene- or 3,7-inter-m-phenylene-3-oxa-$PGF_\alpha$-type compound is transformed to corresponding formula LX PGE-type or formula LXV 11-deoxy-PGE-type compounds. The compounds according to formula LI which are employed as starting material for Chart C are known in the art or readily available by methods known in the art. For example, see U.S. Pat. No. 3,933,900, particularly Chart L therein which describes the preparation of 3,7-inter-m-phenylene-3-oxa-$PGF_{2\alpha}$.

With respect to Chart C, the formula LII compound is prepared form the formula LI compound by cleavage of the 13,14-trans double bond, conveniently by ozonolysis. Ozonolysis proceeds by bubbling dry oxygen, containing about 3 percent ozone, through a mixture of a formula LI compound in a suitable nonreactive diluent. For example, n-hexane is advantageously employed. The ozone may be generated using methods known in the art. See, for example, Fieser, et al., "Reagents for Organic Synthesis," John Wiley and Sons, Inc. (1967), pages 773–777. Reaction conditions are maintained until the reaction is shown to be complete, for example, by silica gel thin layer chromatography or when the reaction mixture no longer rapidly decolorizes a dilute solution of bromine in acetic acid.

The formula LIII compound is prepared from the formula LII compound by acylation, employing methods described above for introducing acyl protecting groups according to $R_9$.

The formula LIV compound is then prepared from the formula LIII compound employing a phosphonate of the formula:

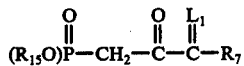

wherein $R_{15}$, $L_1$, and $R_7$ are as defined above. Phosphonates of this general formula are prepared by methods known in the art. See the text hereinabove accompanying Chart A for discussion of the preparation and the appropriate reaction conditions by which the Wittig reaction proceed. The formula LV compound is prepared for the formula LIV compound by transformation of the C-13 to C-14 trans-CH=CH— moiety to a $Y_2$ moiety. Methods discussed in Chart A above are employed.

The formula LV compound is then transformed to the corresponding formula LVI compound by transformation of the 15-keto to an $M_5$ moiety, employing methods described above in Chart A.

Thereafter the formula LVI compound prepared above is transformed to the formula LVII compound by deacylation, employing methods described above for removal of acyl protecting groups according to $R_9$, followed by a chromatographic separation of C-15 epimeric mixtures.

The formula LVII compound is then transformed to the formula LVIII compound and thereafter successively to the formula LIX and formula LX compounds by the methods described in Chart B for the transformation of the formula XLIV compound to the corresponding formula XLVII compound.

This formula LX PGE-type compound is then transformed to the corresponding formula LXV 11-deoxy-PGE-type compound.

The transformation of the formula LX compound to the corresponding formula LXI compound proceeds by acylation. Particularly and especially it is preferred to prepare the formula LXI 11-acetate or 11,15-diacetate. The relatively unstable formula LXI compound is then readily dehydrated yielding the formula LXII PGA-type product. This formula XLII compound is prepared either by allowing the formula LXI compound to spontaneously dehydrate, ordinarily within one to 5 days, or if a more rapid dehydration is required mild acidic conditions, such as exposure to silica gel, are employed.

The formula XLII PGA-type compound is then transformed to the formula LXII 11-deoxy-PGF compounds employing reagents known in the art for the transformation of a PGA compound to corresponding 11-deoxy-PGF compounds. Thus, sodium, potassium, or lithium borohydride at 0°–20° C. are employed. Thereafter, the formula LXIII compound is transformed to the formula LXIV 11-deoxy-PGE-type compound by oxidation. Methods described hereinabove, i.e. in Chart A, for the transformation of PGF-type compounds to corresponding PGE-type compounds are employed. Thus, the Jones reagent or Collins reagent are advantageously used.

Finally, the formula LXV 11-deoxy-PGE-type compound is prepared from the formula LXIV compound by deacylation. Methods described hereinabove for the removal of acyl protecting groups according to $R_9$ are employed.

Chart D provides a method whereby the PGE- or 11-deoxy-PGE-type compounds described in the preceeding Chart are transformed to corresponding formula LXXIV 9-deoxy-9-methylene- or 9,11-dideoxy-9-methylene-PGF-type compounds.

The formula LXXI starting material of Chart D is herein employed, or alternatively, the corresponding 14-halo compound as prepared in Chart A, is employed. Thus, when a 14-halo compound is employed in place of the formula LXXI compound the corresponding 14-halo product corresponding to formula LXXIV is prepared. This 14-halo product is then dehydrohalogenated by the procedure described hereinabove for the dehydrohalogenation of 5,6-dihalo compounds of Chart B. The formula LXXII compound of Chart D is prepared from the formula LXXI compound by silylation of the secondary hydroxyls of the formula LXXI compound. Silylation proceeds by methods known in the art, employing the various silyl groups described in preceeding Charts. See for example Post "Silicones and Other Organic Silicone Compounds," Reinhold Publishing Co., New York, New York (1949) and Pierce, "Silylation of Organic Compounds," Pierce Chemical Co., Rockford, Ill. (1968).

The transformation of the formula LXXII ketone to the corresponding formula LXXIII methylene compound proceeds by methods known in the art. Particularly and especially the procedure disclosed by Johnson, et al., Journal of the America Chemical Society 95, 6462 (1963) is employed.

This procedure first requires the generation of the carbanion of an N-alkyl derivative of an S-methyl-S-arylsulfoximine, for example the carbanion of N,S-dimethyl-S-phenylsulfoximine (i.e., N-methylphenylsulfonimidoylmethyl anion as discussed by Johnson above). This carbanion is generated by reacting the corresponding N-alkyl-S-methyl-S-arylsulfoximine with any of the usual reagents which will extract an active hydrogen from such sulfoximines, for example, an alkyl lithium or alkyl magnesium halide. The formula LXXII compound is then mixed with the carbanion thusly generated, and the resulting material mixed with aluminum amalgam in the presence of acetic acid and water to yield the formula LXXIV product (any silyl groups of the formula LXXIII compound being removed by the acetic acid).

In the above process the use of a slight excess of the N-alkyl-S-aryl-S-methylsulfoximine molecular equivalent of formula LXXII compound is preferred. One molecular equivalent of the hydrogen extracting reagent, e.g. methyl magnesium chloride or butyl lithium, is used for each equivalent of sulfoxamine. The reaction of the carbanion with the formula LXXII compound is carried out in the range of about 0° to −100° C, preferably below about −50° C. An inert reaction diluent is employed, preferably one which is adapted for ease and isolation of reaction products, and is readily miscible with water. Accordingly, tetrahydrofuran is a suitable reaction diluent for the present purposes.

When the reaction of the formula LXXII compound with the carbanion is complete, the resulting product is isolated by procedures known in the art or alternatively the entire reaction mixture is used in the subsequently required reaction with the aluminum amalgam.

This treatment with aluminum amalgam is carried out by contacting the reaction product of the formula LXXII compound and said carbanion with aluminum amalgam advantageously prepared as in Johnson, et al., cited above, in the presence of aqueous acetic acid and at a temperature range of about 0°–50° C., preferably in the range of about 20°–30° C. Other carboxylic acis are alternatively employed in place of acetic acid, for example, propionic acid, butyric acid, and citric acid. Mineral acids, e.g., hydrochloric acid, are also useful for this purpose. The amounts of aluminum amalgam and acetic acid are not critical, provided that sufficient molecular equivalents of each are used to reduce each molecular equivalent of the carbanion-formula LXXII reaction product. The use of a large excess of aluminum amalgam and acid are however preferred. The amount of water present in the reaction mixture is not critical, provided, however, that sufficient water is present to provide an ionizing reaction system. Also, a sufficient quantity of water miscible inert organic diluents is employed to provide a mobile and substantially homogeneous reaction mixtures (except with regard to the aluminum amalgam).

In the event that the preceeding reaction fails to hydrolyze any silyl group at C-11 or C-15, the remaining silyl groups are removed by methods known in the art, e.g., dilute aqueous citric acid, phosphoric acid, and the like. In any event, the formula LXXV compound results.

Chart E provides a method whereby the formula LXXXI compound is lactonized, thereby preparing separable mixtures of the formula LXXII 1,15-lactone and formula LXXIII 1,11-lactone. Further, when $R_8$ is hydrogen, Chart E provides a method whereby the formula LXXXI compound is transformed to the formula LXXXII 9,11-dideoxy-9-methylene-PGF-type, 1,15-lactone. Lactonization herein proceeds by the methods described by Corey, et al., Journal of the American Chemical Society, 96, 5614 (1974), and the application of that method to the prostaglandins is described by Corey, et al., Journal of the American Chemical Society 97, 653 (1975).

Accordingly, the lactones of Chart E are prepared by reacting the formula LXXI compound in anhydrous oxygen-free xylene or benzene, with 2,2'-dipyridyl disulfide, and triphenylphosphine. The pyridine thiol ester thereby formed is lactonized by treatment and refluxing xylene for 2–48 hr.

Mixtures of lactonized products are thereafter separated by conventional methods, e.g. silica gel chromatography or high pressure liquid chromatography.

Chart F provides a method whereby the formula XCI compound prepared according to Chart D is transformed to the formula XCII 2-decarboxy-2-hydroxymethyl compound. This transformation proceeds by methods known in the art for reducing prostaglandins to corresponding primary alcohols. Thus, for example, when the formula XCI compound is an acid or ester, the reduction proceeds with lithium aluminum hydride or diisobutyl aluminum hydride.

Useful reaction diluents include diethyl ether, tetrahydrofuran, dimethoxyethane, or like organic solvents. The reaction mixture is conveniently carried out temperatures of about −78° to 100° C., although preferably at about 0°–50° C.

When the formula XLI compound is an acid, reducing agents such as diborane are also employed, when double bond reduction is not a problem.

Chart G provides a method whereby the formula CI compound, prepared according to Chart D, is transformed to the various 9-deoxy-9-methylene-2-decarboxy-2-aminomethyl or 2-decarboxy-2-(substituted amino)methyl-PGF- or 11-deoxy-PGF-type compounds of formulas CIV, CVI, CVII, CVIII, CIX, or CX By the procedure of Chart G the formula CI compound is transformed to a formula CII mixed acid anhydride. These mixed anhydrides are conveniently prepared from the corresponding alkyl, aralkyl, phenyl, or substituted phenyl chloroformate in the presence of an organic base (e.g., triethylamine). Reaction diluents include water in combination with water miscible organic solvents (e.g., tetrahydrofuran). This mixed anhydride is then transformed to either the formula CIII PG-type, amide or formula CV PG-type azide.

For preparation of the PGF-type, amide (formula CIII) the formula CII mixed acid anhydride is reacted with liquid ammonia or ammonium hydroxide.

Alternatively, the formula CIII compound is prepared from the formula CI free acid by methods known in the art for transformation of carboxy acids to corresponding carboxyamides. For example, the free acid is transformed to a corresponding methyl ester (employing methods known in the art; e.g., excess ethereal diazomethane), and a methyl ester thus prepared is transformed to the formula CIII amide employing the methods described for the transformation of the formula CII mixed acid anhydride to the formula CIII amide.

Thereafter the formula CIV 2-decarobyx-2-aminomethyl-PGF$_{2\alpha}$- or 11-deoxy-PGF$_{2\alpha}$-type compound is prepared from the formula CIII compound by carbonyl reduction. Methods known in the art are employed in this transformation. For example, lithium aluminum hydride is conveniently employed.

The formula CII compound is alternatively used to prepare the formula CV azide. This reaction is conveniently carried out employing sodium azide by methods known in the art. See for example, Fieser and Fieser, Reagents for Organic Synthesis vol. 1, pgs. 1041-1043, wherein reagents and reaction conditions for the azide formation are discussed.

Finally, the formula CVI urethane is prepared from the formula CV azide reaction with an alkanol, aralkanol, phenol, or substituted phenol. For example, when methanol is employed the formula CVI compound is prepared wherein $R_1$ is methyl. This formula CVI PG-type product is then employed in the preparation of either the formula CVII or CVIII product.

In the preparation of the formula CVII primary amine from the formula CVI urethane, methods known in the art are employed. Thus, for example, treatment of the formula CVII urethane with strong base at temperatures above 50° C. are employed. For example, sodium potassium or lithium hydroxide is employed.

Alternatively, the formula CVI compound is employed in the preparation of the formula CVIII compound. Thus, when $L_1$ is alkyl the formula CVIII compound is prepared by reduction of the formula CVI urethane wherein $R_1$ is alkyl. For this purpose, lithium aluminum hydride is the conveniently employed reducing agent.

Thereafter, the formula CVIII product is used to prepare the corresponding CIX urethane by reaction of the formula CVIII secondary amine (wherein $L_2$ is alkyl) with an alkyl chloroformate. The reaction thus proceeds by methods known in the art for the preparation of carbamates from corresponding secondary amines. Finally, the formula CX product wherein $L_2$ and $L_3$ are both alkyl is prepared by reduction of the formula CIX carbamide. Accordingly, methods hereinabove described for the preparation of the formula CVIII compound from the formula CVI compound are used. Optionally, the various reaction steps herein are proceeded by the employment of blocking groups according to $R_{10}$, thus necessitating their subsequent hydrolysis in preparing each of the various products above. Methods described hereinabove for the introduction and hydrolysis of blocking groups according to $R_{10}$ are employed.

Finally, the processes described above for converting the formula CII compound to the formula CV compound and the various compounds thereafter, result in shortening the 8α-side chain of the formula CI compound by one carbon atom. Accordingly, the formula CI starting material should be selected so as to compensate for the methylene group which is consumed in the steps of the above synthesis. Thus, where a 2α-homo-product is desired a corresponding formula CI 2a,2b-dihomo starting material must be employed. Starting materials containing an additional methylene group in the formula CI compound between the $Z_1$ moiety and the carboxyl are prepared by methods known in the art or procedures described in Charts A through C. For example, Wittig reagents containing an additional methylene are known in the art or prepared by methods described above.

Optically active PG-type products are obtained from optically active intermediates, according to the process steps of the above charts. Likewise optically active PG-type compounds are obtained from corresponding optically active PG-type compounds following the procedures in the above charts. When racemic intermediates are used in the reactions above, racemic products are obtained. These products may be used in their racemic form or if preferred they may be resolved as optically active enantiomers following procedures known in the art. For example, when a PG-type free acid is obtained, the racemic form thereof is resolved into d and l forms by reacting said free acid by known procedures with an optically active base (e.g., brucine or strychnine) thereby yielding a mixture of 2 diastereomers which are separable by procedures known in the art (fractional crystallization to yield the separate diastereomeric salts). The optically active acid may then be prepared from the salt by general procedures known to the art.

In all of the above described reactions, the products are separated by conventional means from starting material and impurities. For example, by use of silica gel chromatography monitored by thin layer chromatography the products of the various steps of the above charts are separated from the corresponding starting materials and impurities.

As discussed above, the processes herein described lead variously to carboxylic acids ($R_1$ is hydrogen) or to esters when preparing novel analogs wherein $X_1$ is —COOR.

When the alkyl ester has been obtained and an acid is desired, saponification procedures, as known in the art for PGF-type compounds are employed.

For alkyl esters of PGE-type compounds enzymatic processes for transformation of esters to their acid forms may be used by methods known in the art when saponification procedures would cause dehydration of the prostaglandin analog. See for reference E. G. Daniels, Process For Producing An Esterase, U.S. Pat. No. 3,761,356.

When an acid has been prepared and an alkyl, cycloalkyl, or aralkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N.Y. Vol. 8, pp. 389-394 (1954).

An alternative method for alkyl, cycloalkyl or aralkyl esterification of the carboxy moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Various methods are available for preparing phenyl or substituted phenyl esters within the scope of the invention from corresponding aromatic alcohols and the free acid PG-type compounds, differing as to yield and purity of product.

Thus by one method, the PG-type compound is converted to a tertiary amine salt, reacted with pivaloyl halide to give the mixed acid anhydride and then reacted with the aromatic alcohol. Alternatively, instead of pivolyl halide, an alkyl or arylsulfonyl halide is used, such as p-toluenesulfonyl chloride. See for example Belgian Patents 775,106 and 776,294, Derwent Farmdoc Nos. 33705T and 39011T.

Still another method is by the use of the coupling reagent, dicyclohexycarbodiimide. See Fieser et al., "Reagents for Organic Synthesis," pp. 231-236, John Wiley and Sons, Inc., New York, (1967). The PG-type compound is contacted with one to ten molar equivalents of the aromatic alcohol in the presence of 2-10 molar equivalents of dicyclohexylcarbodiimide in pyridine as a solvent.

One preferred novel process for the preparation of these esters, however, comprises the steps:
 a. forming a mixed anhydride with the PG-type compound and isobutylchloroformate in the presence of a tertiary amine and
 b. reacting the anhydride with an appropriate aromatic alcohol.

The mixed anhydride described above is formed readily at temperatures in the range −40° to +60° C., preferably at −10° to +10° C. so that the rate is reasonably fast and yet side reactions are minimized. The isobutylchloroformate reagent is preferably used in excess, for example 1.2 molar equivalents up to 4.0 per mole of the PG-type compound. The reaction is preferably done in a solvent and for this purpose acetone is preferred, although other relatively nonpolar solvents are used such as acetonitrile, dichloromethane, and chloroform. The reaction is run in the presence of a tertiary amine, for example triethylamine, and the co-formed amine hydrochloride usually crystallizes out, but need not be removed for the next step.

The aromatic alcohol is preferably used in equivalent amounts or in substantial stoichiometric excess to insure that all of the mixed anhydride is converted to ester. Excess aromatic alcohol is separated from the product by methods described herein or known in the art, for example by crystallization. The tertiary amine is not only a basic catalyst for the esterification but also a convenient solvent. Other examples of tertiary amines useful for this purpose include N-methylmorpholine, triethylamine, diisopropylethylamine, and dimethylaniline. Although they are effectively used, 2-methylpyridine and quinoline result in a slow reaction. A highly hindered amine such as 2,6-dimethyllutidine is, for example, not useful because of the slowness of the reaction.

The reaction with the anhydride proceeds smoothly at room temperature (about 20° to 30° C.) and can be followed in the conventional manner with thin layer chromatography (TLC).

The reaction mixture is worked up to yield the ester following method known in the art, and the product is purified, for example by silica gel chromatography.

Solid esters are converted to a free-flowing crystalline form on crystallization from a variety of solvents, including ethyl acetate, tetrahydrofuran, methanol, and acetone, by cooling or evaporating a saturated solution of the ester in the solvent or by adding a miscible nonsolvent such as diethyl ether, hexane, or water. The crystals are then collected by conventional techniques, e.g. filtration or centrifugation, washed with a small amount of solvent, and dried under reduced pressure. They may also be dried in a current or warm nitrogen or argon, or by warming to about 75° C. Although the crystals are normally pure enough for many applicants, they may be recrystallized by the same general techniques to achieve improved purity after each recrystallization.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to disclose an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is than added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaterary ammonium are produced by mixing an acid of this invention with the stoichiometric amount of the corresponding quaternary ammonium hydroxide in water solution, followed by evaporation of the water.

The acids or esters of this invention prepared by the processes of this invention are transformed to lower alkanoates by interaction of a free hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutryic anhydride, or hexanoic anhydride gives the corresponding carboxyacylate.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, and T-60 spectrophotometer on deuterochloroform solutions with tetramethylsilane as an internal standard (downfield).

Mass spectra are recorded on a CEC model 21-110B Double Focusing High Resolution Mass Spectrometer on an LKB Model 9000 Gas-Chromatograph-Mass Spectrometer. Trimethylsilyl derivatives are used, except where otherwise indicated.

The collection of chromatographic eluate fractions starts when the eluant front reaches the bottom of the column.

"Brine", herein, refers to an aqueous saturated sodium chloride solution.

The A-IX solvent system used in thin layer chromatography is made up from ethyl acetate-acetic acid-cyclohexane-water (90:20:50:100) as modified from M. Hamberg and B. Samuelsson, J. Biol. Chem. 241, 257 (1966).

Skellysolve-B (SSB) refers to mixed isometric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

DDQ refers to 2,3-dichloro-5,6-dicyano-1,4-benzoquinone. Preparation 1 cis-4,5-Didehydro-17-phenyl-18,19,20-trinor-14-chloro-PGE$_1$ (Formula XXXVIII: Z$_2$ is cis-CH$_2$—CH=CH—(CH$_2$)$_2$-; R$_1$ is hydrogen R$_8$ is hydroxy; M$_1$ is

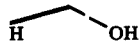

R$_3$ and R$_4$ of the L$_1$ moiety are hydrogen and R$_7$ is benzyl).

Refer to Chart A.

A. A solution of 24.3 g. of thallous ethoxide in 125 ml. of dry benzene is cooled in an ice bath, and thereafter a solution of 25.3 g. of methyl 2-oxo-4-phenylbutyl phosphonate in 75 ml. of benzene is added and thereafter rinsed with 50 ml. of benzene. The solution is stirred for 30 min, at 5° C. and thereafter 22.1 g. of crystalline 3α-benzoyloxy-5α-hydroxy-2β-carboxadehyde-1α-cyclopentane-acetic acid, γ-lactone (formula XXI) is added rapidly. This reaction mixture is then stirred for 13 hours at ambient temperature yielding a brown solution of pH 9—10. Acetic acid (6 ml.) is added and the mixture is transferred to a beaker with 600 ml. of diethyl ether. Celite and 500 ml. of water is added, followed by the addition of 30 ml. (about 33 g.) of saturated potassium iodide. The mixture (containing a bright yellow precipitate of thallous iodide) is stirred for about 45 min., and thereafter filtered through a bed of Celite. The organic layer is then washed with water, aqueous potassium bicarbonate, and brine. Thereafter the resulting mixture is dried over magnesium sulfate and evaporated at reduced pressure, yielding crude formula XX product, which is then chromatographed on 600 g. of silica gel packed in 20 percent ethyl acetate in cyclohexane. Elution, collecting 500 ml. fractions, with 2 l. of 20 percent, 2 l. of 25 percent, and 4 l. of 30 percent ethyl acetate in cyclohexane yields purified product, 3α-benzoyloxy-5α-hydroxy-2α-(3-oxo-5-phenyl-trans-1-pentenyl)-1α-cyclopentaneacetic acid, γ-lactone.

Alternatively this product is prepared by adding 3α-benzoyloxy-2β-carboxaldehyde-5α-hydroxy-1α-cyclopentaneacetic acid γ-lactone (3 g.) in 30 ml. of dichloromethane to a solution of dimethyl 2-oxo-(4-pentylbutylphosphonate) (6.69 g.) and sodium hydride (1.35 g.) in 15 ml. of tetrahydrofuran. The resulting reaction mixture is then stirred for 2 hours at about 25° C., acidified with acetic acid, and concentrated under reduced pressure. The residue is partitioned between dichloromethane and water, and the organic phase is concentrated. The residue is chromatographed on silica gel, eluting with ethyl acetate in Skelly-solve B (1:1).

B. A solution of the reaction product of part A of this example (1.15 g.) in dioxane (35 ml.) is treated with N-chlorosuccinimide (9.7 g.) and stirred for 6 days. The resulting solution is then diluted with methylene chloride, washed with saline and a sodium sulfate solution, dried, and evaporated to yield a residue. The residue in benzene is subjected to silica gel chromatography, eluting with hexane and ethyl acetate (9:1) whereupon pure 3α-benzoyloxy-5α-hydroxy-2β-(1,2-dichloro-3-oxo-4-phenylpentyl)-1α-cyclopentaneacetic acid γ-lacetone is recovered (as a mixture of isomers). Thereafter the dichlorides so obtained are diluted with pyridine (20 ml.) and heated at 100 C. for 4.5 hours. The resulting solution is then diluted with diethyl ether and washed with ice cold dilute hydrochloric acid and brine. The resulting mixture is then dried and subject to silica gel chromatography, eluting with hexane and ethyl acetate (9:1), yielding pure formula XXIII product (Y$_2$ is trans—CH=CCl—) product.

Alternatively, the reaction product of part A above (0.190 g.) in dry pyridine (5 ml.) at 0° C. is treated with freshly distilled sulfuryl chloride (0.386 g.) and the reaction is maintained for 5 hours. Thereafter additional sulfuryl chloride (0.667 g.) and pyridine (5 ml.) is added and the reaction continued for 12 hours for ambient temperature. The resulting solution is then diluted with methylene chloride, washed with ice cold phosphoric acid, sodium bicarbonate, dried, and evaporated. The residue is chromatographed on silica gel eluting with hexane and ethyl acetate (9:1). Pure product identical with that recovered in the preceding paragraph is obtained.

C. Sodium borohydride (0.92 g.) is slowly added to a stirred suspension of 2.1 g. of anhydrous zinc chloride in 45 ml. of dimethyl ether in ethylene glycol (glyme) with ice bath cooling. The mixture is stirred for 20 hours at ambient temperature and thereafter cooled to −18° C. A solution of 0.76 g. of 3α-benzoyloxy-5α-hydroxy-2β-(2-chloro-3-oxo-4-phenyl-trans-1-pentenyl)-1α-cyclopentaneacetic acid γ-lactone (prepared according to part B) in 12 ml. of glyme is added over a period of 20 minutes. Stirring is continued for 24 hours at −20° C. and thereafter 40 ml. of water is cautiously added. The reaction mixture is warmed to room temperature, diluted with ethyl acetate, and washed twice with brine. The aqueous layers are extracted with ethyl acetate. The combined organic extracts are dried over sodium sulfate and evaporated to yield crude product, which when chromatographed on 120 g. of silica gel eluting with hexane and in ethyl acetate (3:1) yields the epimerically pure (15R) or (15S) formula XXIV title product.

D. A solution of 100 mg. of the reaction product of part C in 20 ml. of methanol is purged with nitrogen. Thereafter, potassium carbonate (30 mg.) is added and the resulting mixture is stirred at ambient temperature until thin layer chromatographic analysis shows the solvolysis to be complete (about 12 hours). The solution is then diluted with ice water and neutralized with cold, dilute phosphoric acid. The resulting mixture is then dried and evaporated under reduced pressure. The residue is then chromatographed using silica gel eluting with hexane and ethyl acetate (3:2). Accordingly, the deacylated formula XXB lactone is prepared.

E. A solution of 0.39 g. of the reaction product of part D above, in 25 ml. of methylene chloride (containing 1.2 ml. of dihydropyran and 1.2 mg. of pyridine hydrochloride is allowed to stand for one hour at ambient temperature. Additional dihydropyran (1.2 ml.) is added and the reaction continued for 36 hrs. The reaction mixture is then washed with water, aqueous sodium bicarbonate, dried, and evaporated, yielding the formula XXVI bis-tetrahydropyranyl lactone corresponding to the lactone reaction product of part A above.

F. A solution of the reaction product of part E above (0.39 g.) in 10 ml. of toluene is cooled to −70° C. and thereafter 10 ml. of 10 percent diisobutylaluminum hydride (1.64 mmoles) in toluene (10 ml.) is slowly added. The reaction mixture is then stirred at −70° C. until thin layer chromatographic analysis indicates that the reduction is complete (about 10 min.). Thereafter the cooling bath is removed and 9 ml. of a mixture of tetrahydrofuran and water (3:1) is added slowly. The reaction mixture is then stirred and allowed to warm to room temperature, and is then filtered through a cellulose bed. The filter cake is rinsed with benzene, combined organic extracts are then dried and evaporated to yield the formula XXVII lactol.

G. A suspension of methoxymethyltriphenylphosphonium chloride (32.5 g.) in 150 ml. of tetrahydrofuran is cooled to −5° C. To the suspension is added 69.4 ml. of n-butyllithium in hexane (1.6 molar) in 45 ml. of tetrahydrofuran. After 30 min. there is added a solution of the reaction product of part F, 3α,5α-dihydroxy-2β-[2-chloro-(3R)-3-hydroxy-5-phenyl-trans-1-pentenyl]-1α-cyclopentaneacetaldehyde γ-lactol bis-(tetrahydropyranyl)ether, (10 g.), in 90 ml. of tetrahydrofuran. The mixture is stirred for 1.5 hrs. while warming to 25° c. The resulting solution is thereafter concentrated under reduced pressure. The residue is partitioned between dichloromethane and water, the organic phase being dried and concentrated. This dry residue is then subjected to chromatography over silica gel eluting with cyclohexane and ethyl acetate (2:1). Those fractions as shown by thin layer chromatography to contain pure formula XXVIII product are combined.

H. The reaction product of part G above in 20 ml. of tetrahydrofuran is hydrolyzed with 50 ml. of 66 percent aqueous acetic acid at about 57° C. for 2.5 hrs. The resulting mixture is then concentrated under reduced pressure. Toluene is added to the residue and the solution is again concentrated. Finally the residue is subjected to chromatography on silic gel, eluting with chloroform and methanol (6:1). The title compound is thereby obtained by combining and concentrating fractions as shown by thin layer chromatography to contain pure product. Accordingly, there is obtained the corresponding formula XXIX δ-lactol.

I. Silver oxide is prepared by the addition of silver nitrate (1.14 g.) in water (3 ml.) dropwise to a 2 normal sodium hydroxide solution (6.8 ml.). A precipitate is formed. Added to the precipitate in ice water bath is the δ lactol of part H above (1 g.) in tetrahydrofuran (4 ml.). When the addition is complete, the ice bath is removed and the reaction mixture allowed to warm to ambient temperature. When the reaction is complete, as shown by thin layer chromatography (chloroform and methanol), (9:1), impurities are removed by filtration. the filtrate is then extracted with diethyl ether. The aqueous layer is then chilled in an ice bath and acidified with 10 percent potassium bisulfate solution to pH less than 2. This aqueous mixture is then extracted with diethyl ether. The ethereal extracts are then combined, washed with brine, dried over magnesium sulfate, filtered, and evaporated under reduced pressure to yield the formula XXX lactone.

J. The formula XXX lactone prepared in part I above is then transformed to its formula XXXI bis-tetrahydropyranyl ether derivative following the procedure described in part E.

K. The formula XXXI compound prepared in part J above is then reduced to the corresponding δ]lactol bistetrahydropyranyl ether by the procedure described in part F.

L. 3-Carboxpropyltriphenylphosphonium bromide (prepared by heating 4-bromobutyric acid and triphenylphosphine in benzene at reflux for 18 hours, and thereafter purifying), 106 g., is added to sodiomethylsulfinylcarbanide prepared from sodium hydride (2.08 g., 57 percent) and 30 ml. of dimethylsulfoxide. The resulting Wittig reagent is combined with the formula XXXII lactol (n is 2) of part K above and 20 ml. of dimethylsulfoxide. The mixture is stirred overnight, diluted with about 200 ml. of benzene, and washed with potassium hydrogen sulfate solution. The two lower layers ae washed with dichloromethane, the organic phases are combined, washed with brine, dried, and concentrated under reduced pressure. The residue is subjected to chromatography over acid washed silica gel, eluting with ethyl acetate. Those fractions shown to contain the formula XXV cis-4,5-didehydro-PGF$_{1\alpha}$ compound by thin layer chromatography are combined to yield pure product.

M. A solution of cis-4,5-didehydro-17-phenyl-18,19,20-trinor-14-chloro-PGF$_{1\alpha}$, 11,15-bis-tetrahydropyranyl ether, prepared in Part L above, in 60 ml. of acetone is cooled to −25° C. Thereupon 1.9 ml. of Jones reagent is added. The reaction mixture is then stirred for 25 min. at −25° C. and isopropyl alcohol (1.9 ml.) is added after an additional 15 min. at −25° C. the reaction mixture is diluted with 200 ml. of water (0° C.) and extracted with diethyl ether. Ethereal extracts are washed with 75 ml. of cold 0.1 N potassium bicarbonate 150 ml. of brine, dried over magnesium sulfate, and evaporated, thereby yielding cis-4,5-didehydro-17-phenyl-18,19,20-trinor-14-chloro-PGE$_1$, 11,15-bis-tetrahydropyranyl ether, a formula XXXVII compound.

N. A solution of the crude product of part m above is reacted with 16 ml. of tetrahydrofuran, water, and acetic acid (1:3:6) and allowed to stand at 40° C. for 4 hrs. The resulting mixture is thereafter diluted with 120 ml. of water and freeze dried. The residue is dissolved in diethyl ether and washed with potassium bicarbonate, brine, and thereafter dried and evaporated to yield crude product. The crude product is chromatographed on 25 g. of silica gel packed in 5 percent acetone in methylene chloride. Elution with 5 to 40 percent acetone in methylene chloride yields the pure formula XXXVIII title product.

Preparation 2 5,6-Didehydro-PGE$_2$, methyl ester (Formula XLVII: Z$_5$ is —C≡C—(CH$_2$)$_3$—; R$_8$ is hydroxy, Y$_1$ is trans-CH═CH—, R$_3$ and R$_4$ of the L$_1$ moiety and R$_5$ of the M$_1$ moiety are all hydrogen, R$_1$ is methyl, and R$_7$ is n-butyl).

Refer to Chart B.

A. PGF$_{2\alpha}$, methyl ester (formula XLI, 4.56 g.) and 20 ml. of pyridine is subjected to dropwise addition of 4.0 g. of benzoyl chloride. The reaction mixture is then stirred at 25° C. for 16 to 24 hr. The reaction mixture is then cooled to 0° C., adding 5 ml. of water, stirring for 10 min., and thereafter extracting with diethyl ether. The ethereal layers are then washed with sodium bisulfate, sodium bicarbonate, and brine; dried over anhydrous magnesium sulfate; filtered; and concentrated under reduced pressure to yield crude formula XLII tribenzoate which is purified by high pressure liquid chromatography.

B. The reaction product of part A (5.9 g.) and 5 mg. of potassium carbonate are dissolved in 200 ml. of chloroform stirring under a nitrogen atmosphere at −20° C. Thereafter 1.6 g. of bromine in 10 ml. of chloroform is added over a period of 10 min. The reaction mixture is stirred for an additional 15 min. and concentrated under reduced pressure. The product thus obtained (the 5,6-dibromo- derivative of the tribenzoate starting material is then reacted in a solution containing 15.2 g. of 1,5-diazobicyclo-[5.4.0]-undec-5-ene (DBU) in 40 ml. of dioxane at 100° C. The reaction is maintained under a nitrogen atmosphere for 7 hr. and thereafter cooled to 25° C. for an additional 16 hr. The resulting mixture is then acidified with sodium bisulfate and extracted with 2 l. of diethyl ether. The ethereal layer is then washed with sodium bisulfate, sodium bicarbonate, and brine, and dried over anhydrous magnesium sulfate. Concentration under reduced pressure yields crude formula XLIII 5,6-didehydro-PGF$_{2\alpha}$, methyl ester, tribenzoate.

C. The crude product of part B is placed in a solution of 250 ml. of 2 percent potassium carbonate in methanol and stirred at 25° C. for 24 hr. The resulting mixture is then acidified to pH 4 or 5 with sodium bisulfate and concentrated to a residue which is extracted with ethyl acetate. The ethyl acetate extracts are then washed with brine and dried over anhydrous magnesium sulfate. The resulting mixture is then concentrated under vacuum with excess ethereal diazomethane added to esterify a partially hydrolyzed free acid. This product is then purified by high pressure liquid chromatography using ethyl acetate and chloroform (2:1) as solvent, yielded 5,6-didehydro-PGF$_{2\alpha}$, methyl ester, formula XLIV.

D. The methyl ester of part D (439.2 mg.) in 1.2 ml. of dimethylformamide are cooled to 0°-5° C. and thereafter 450 mg. of t-butyldimethylsilane and 408 mg. of imidazole in 1.2 ml. of dimethylformamide is added. This mixture is allowed to stand for 24 hr. at 0°-5° C. The mixture is then stirred with addition of 1 to 2 ml. of water. After 10 min. the resulting mixture is extracted with diethyl ether and hexane (1:1). The organic layer is washed with sodium bisulfate, and brine and dried over anhydrous magnesium sulfate. Concentration under reduced pressure yields crude product. Chromatography yields per formula XLV bis-(t-butyldimethylsilyl ether) product.

E. 618 mg. of pyridine and 10 ml. of methylene chloride are combined with 390 mg. of chromic acid which mixture is then stirred for 15 min. Thereafter the reaction product of part D (385 mg.) in 3.5 ml. of methylene chloride is added and stirring is continued for one hr. The layers are then separated and a tar-containing layer is washed well with diethyl ether, and these combined ethereal layers are then washed with sodium bisulfate, sodium bicarbonate, sodium bisulfite, and brine and dried over anhydrous sodium sulfate. Filtration and concentration under vacuum yields crude 5,6-didehydro-PGE$_2$, 11,15-bis(t-butyldimethylsilyl ether), methyl ester (formula XLVI).

F. The crude product from part E is hydrolyzed in 6.5 ml. of a mixture of tetrahydrofuran water and trifluoroacetic acid (8:2:1) at 25° C. After 7 hr. the reaction mixture is neutralized by addition of saturated sodium bicarbonate (adjusted pH to 7 to 8) and is stirred for 30 min. at 25° C. The reaction mixture is then extracted with chloroform and the chloroform extract is washed with sodium bicarbonate and brine and dried over anhydrous magnesium sulfate. Concentration under reduced pressure yields crude formula XLVII title product, which is then purified using preparative thin layer chromatography (chloroform and acetone 2:1).

Preparation 3 3,7-inter-m-phenylene-3-oxa-16-phenoxy-4,5,6,17,18,19,20-heptanor-11-deoxy-PGE$_1$ (Formula LXV: R$_1$ is hydrogen, Z$_3$ is oxa, Y$_1$ is trans—CH═CH—, R$_3$ and R$_4$ of the L$_1$ moiety and R$_5$ of the M$_1$ moiety are all hydrogen and R$_7$ is phenoxy, and g is one).

Refer to Chart C.

A. 3,7-inter-m-phenylene-3-oxa-4,5,6-trinor-PGF$_{1\alpha}$, methyl ester (10 g.) in 200 ml. of methanol is cooled to 0° C. in an ice-bath. A stream of ozone, generated from a conventional ozone-producing apparatus, is passed through the mixture until the starting material is completely consumed. Thereupon, the resulting mixture is washed and concentrated, and the residue chromatographed, yielding pure formula LII aldehyde.

B. Following the procedure of Preparation 2, part A, the reaction product of part A above is transformed to the formula LIII dibenzoate.

C. Following the procedure of Preparation 1, part A, but employing dimethyl 2-oxo-3-phenoxypropylphosphonate, the reaction product of part B above, is transformed to the formula LIV compound.

D. Following the procedure of Preparation 1, part C, the reaction product of part C above is transformed to a formula LVI compound.

E. Following the procedure of Preparation 2, part C, the reaction product of part D above is transformed to a formula LVII compound.

F. Following the procedure of Preparation 2, part D, the reaction product of part E above is transformed to a formula LVIII compound.

G. Following the procedure of Preparation 2, part E, the reaction product of part F above is transformed to a formula LIX compound.

H. Following the procedure of Preparation 2, part F, the reaction product of part G above is transformed to a formula LX compound.

I. To a stirred solution of the reaction product of part H above in 3.3 ml. of dry pyridine at ambient temperature under a nitrogen atmosphere is added one ml. of acetic anhydride. After 2.5 hr. the reaction mixture is cooled to 0° C. and 3.3 ml. of methanol are added. The reaction mixture is then stirred for 5 min. at 0° C. and for 18 hr. at ambient temperature. The reaction is then quenched by addition of an equilibrated mixture of sodium bisulfate, ice, and diethyl ether. The aqueous extract is then washed well with diethyl ether and the organic extract is combined, washed with water, saturated sodium bicarbonate, and brine. The resulting mixture is thereafter dried over sodium sulfate and evaporated to yield the formula LXI 11,15-diacetate.

J. Crude reaction product of part I above is chromatographed on silica gel packed in ethyl acetate, eluting with 50 percent ethyl acetate and hexane. Fractions shown to contain pure formula LXII compound by thin layer chromatography are combined.

K. To a stirred solution of the reaction product of step J above, dissolved in methanol, at −20° C. under a nitrogen atmosphere there is added sodium borohydride and a mixture of water and methanol. The resulting mixture is then stirred at −20° C. for 20 min. and thereafter acetic acid is added, quenched in the reaction.

This resulting mixture is then concentrated and water and citric acid are added, adjusting the pH to about 3. This mixture is then extracted with dichloromethane and the combined extracts are washed with water and brine, dried and concentrated to yield a formula LXXIII compound.

L. A solution of the reaction product of step K dissolved in acetone is combined, by dropwise addition, with stirring over a period of about one min. with one equivalent of Jones reagent (chromium trioxide, water, and concentrated sulfuric acid). The resulting mixture is stirred at −20° C. for 20 min. and thereafter isopropanol is added, quenching the reaction. The resulting mixture is stirred at −20° C. for 10 min. and thereafter diluted with water and extracted with diethyl ether. The combined extracts are washed with water and brine dried and concentrated. The residue is then chromatographed on silica gel and those fractions as shown by thin layer chromatography to contain pure formula LXIV product are combined.

M. To a solution of the reaction product of step L above, dissolved in methanol, there is added aqueous sodium hydroxide, and the resulting mixture stirred at ambient temperature for 17 hr. The resulting mixture is then acidified with 3N hydrochloric acid and concentrated to an aqueous residue. The residue is diluted with 25 ml. of water and extracted with diethyl ether. The combined extracts are then washed with brine, dried, and concentrated. The residue is then chromatographed on silica gel, yielding pure formula LXV product, a free acid.

Following procedures generally described in Preparations 1-3, but employing appropriate starting material and reactants, there are prepared each of the various formula LXXI compounds, or their corresponding 14-chloro analogs, except those wherein $Z_1$ is —CH$_2$—O—CH$_2$—(CH$_2$)$_g$—CH$_2$—. These compounds, the 5-oxa-PGE-type formula LXXII compounds, are obtained by methods described in U.S. Pat. No. 3,864,387.

EXAMPLE 1 cis-4,5,13,14-Tetrahydro-17-phenyl-18,19,20-trinor-9-deoxy-9-methoxy-PGF$_1$, methyl ester (Formula LXXIV: $R_1$ is methyl, $Z_1$ is cis—CH$_2$—CH═CH—(CH$_2$)$_2$—, $R_8$ is hydroxy, $Y_1$ is —C≡C—, $R_3$ and $R_4$ of the $L_1$ moiety, and $R_5$ of the $M_1$ moiety are all hydrogen, and $R_7$ is benzyl).

Refer to Chart D.

A. A solution of the methyl ester of Preparation 1 (300 mg., prepared by ethereal diazomethane esterification) in 15 ml. of tetrahydrofuran, containing 3 ml. of hexamethyldisilazane and 0.75 ml. of trimethylchlorosilane is stirred at ambient temperature for about 5 hr. Following removal of solvents under reduced pressure, the residue is taken up in 50 ml. of xylene, filtered through Celite, and concentrated under reduced pressure to yield a 14-chloro analog of a compound of formula LXXII.

B. A tetrahydrofuran solution of methyl magnesium chloride (50 ml.; 2M) is added dropwise during 20 min. to a stirred solution of N,S-dimethyl-S-phenylsulfoximine (17 g.) in 150 ml. of anhydrous tetrahydrofuran at 0° C. The resulting mixture is then stirred for 15 min. at 0° C. and is thereafter maintained at 0° C. being added to a stirred solution of the reaction product of part A (18 g.) and 65 ml. of tetrahydrofuran at about −78° C. Addition continues over about 35 min. Stirring is continued at −78° C. for 2.5 hr. thereafter. The resulting mixture is then poured into saturated aqueous ammonium chloride (500 ml.) ice, and diethyl ether. The resulting mixture is extracted with diethyl ether and the combined extracts are washed with brine and dried over sodium sulfate. Removal of diethyl ether under reduced pressure yields a residue which is dissolved in 200 ml. Aqueous citric acid is then added to the methanol containing solution and the resulting mixture stirred for 30 min. at ambient temperature. Brine is added and the mixture is extracted several times with methyl acetate. The combined extracts are then washed with brine, dried over sodium sulfate, and evaporated under reduced pressure to yield a residue.

The residue from the preceeding paragraph is dissolved in 900 ml. of tetrahydrofuran. To this solution is added with stirring 140 ml. of water, 140 ml. of acetic acid, and amalgamated aluminum prepared from 30 g. of 20 mesh aluminum metal granules. This mixture is maintained at about 20° to 25° C. After stirring for one hr., Celite is added, and the mixture is filtered through a pad of Celite. The filter pad is washed with three 150 ml. portions of tetrahydrofuran and the combined filtrate and washings are evaporated under reduced pressure. Brine is added to the residue and the mixture is extracted with ethyl acetate and hexane (4:6). Combined extracts are then washed with 150 ml. portions of brine and thereafter with 0.5 M aqueous disodium hydrogen phosphate until pH 9 is achieved. Then the combined extracts are washed with brine, dried over sodium sulfate and evaporated to yield a residue which is chromatographed on silica gel, yielding the 14-chloro analog of the formula LXXIV compound.

C. The reaction product of part B is transformed to the title product by dehydrohalogenation, following the procedure described in Preparation 2, part B.

EXAMPLE 2

5,6-Didehydro-9-deoxy-9-methylene-PGF$_2$, methyl ester (Formula LXXIV: R$_1$ is methyl, Z$_1$ is —C≡C—(CH$_2$)$_3$—, R$_8$ is hydroxy, Y$_1$ is trans—CH=CH—, R$_3$ and R$_4$ of the L$_1$ moiety and R$_5$ of the M$_1$ moiety are all hydrogen, and R$_7$ is n-butyl).

Refer to Chart D.

A. Following the procedure of Example 1, part A, the reaction product of Preparation 2 is silylated, yielding a formula LXXII compound.

B. Following the procedure of Example 1, part B, the reaction product of part A above is transformed to the title product.

EXAMPLE 3

3,7-inter-m-phenylene-3-oxa-16-phenoxy-4,5,6,17,18,19,20-heptanor-9,11-dideoxy-9-methylene-PGF$_1$, methyl ester (Formula LXXIV: R$_1$ is methyl, Z$_1$ is

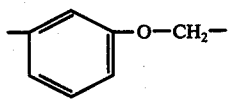

R$_8$ is hydrogen, Y$_1$ is trans—CH=CH—, R$_2$ and R$_4$ of the L$_1$ moiety and R$_5$ of the M$_1$ moiety are all hydrogen, and R$_7$ is

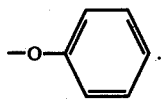

Refer to Chart D.

A. The method ester of the title product of Preparation 3 (prepared by ethereal diazomethane esterification) is transferred to a formula LXXXII 15-silyl derivative following the procedure of Example 1, part A.

B. Following the procedure of Example 1, part B, the reaction product of part A above is transformed to the title product.

EXAMPLE 4

9-Deoxy-9-methylene-PGF$_1$ (Formula LXXIV: R$_1$ is hydrogen, Z$_1$ is —(CH$_2$)$_5$—, R$_8$ is hydrogen, R$_3$ and R$_4$ of the L$_1$ moiety and R$_5$ of the M$_1$ moiety are all hydrogen, and R$_7$ is n-butyl) or its methyl ester.

Refer to Chart D.

A. Following the procedure of Example 1, part A, 10.5 g. of PGE$_1$, methyl ester, 360ml. tetrahydrofuran, 144 ml. of hexamethyldisilizane and 29.8 ml. of chlorotrimethylsilane are reacted to yield PGE$_1$, methyl ester, 11,15-bis-(trimethylsilyl ether).

B. Following the procedure of Example 1, part B, 11.4 g of the reaction product of part A and 8.55 g. of N,S-dimethyl-S-phenylsulfoximine and 16.7 ml. of 3M solution of methyl magnesium chloride in tetrahydrofuran are reacted yielding a product isolated by the procedure of Example 1, part B. This isolated product is then transformed to the title methyl ester by reaction with 70 ml. of 2.5 percent aqueous citric acid, aluminum amalgam prepared from 21 g. of 20 mesh aluminum and 21 g. of mercuric chloride in water.

C. The methyl ester prepared in part B above is (750 mg.) is saponified by reaction with 9 ml. of 3N aqueous sodium hydroxide in 15 ml. of methanol. The mixture is stirred under a nitrogen atmosphere for about 1.5 hr. at ambient temperature and thereafter poured into a mixture of brine and ice and the free acid prepared therefrom by acidification with sodium bisulfate. Ethyl acetate extracts of the resulting mixture are washed with brine and dried over sodium sulfate and evaporated to yield the residue which is crystallized from ethyl acetate ether and hexane. Accordingly, there are obtained 857 mg. of the title product. Melting point is 62°–63° C. Infrared absorptions are observed at 3400, 3200, 2760, 1740, 1650, 1380, 1220, 1160, 1070, 904, 860, and 725 cm.$^{-1}$. NMR absorptions are observed at 5.8–5.35, 5.5–4.7, and 4.25–3.50 δ. The mass spectrum exhibits a parent peak at 568.3810 and other peaks at 553, 497, 478, 463, 407, 199, 173, and 117.

EXAMPLE 5

9-Deoxy-9-methylene-PGF$_1$, 1,15-lactone (Formula LXXXII: Z$_1$, R$_8$, Y$_1$, R$_5$, L$_1$, and R$_7$ are as defined in Example 4) and 1,11-lactone (Formula LXXXIII: Z$_1$, Y$_1$, M$_1$, L$_1$, and R$_7$ are as defined in Example 4).

Refer to Chart E.

A mixture of 9-deoxy-9-methylene-PGF$_1$ (352 mg.), 393 mg. of triphenylphosphine and 330 mg. of 2,2'-dipyridylsulfide and 5 ml. of dry oxygen free xylene is stirred under a nitrogen atmosphere at room temperature for 18 hr. The reaction mixture is then diluted with 250 ml. of xylene and treated at reflux until thin layer chromatographic analysis indicates the starting material is completely consumed. The xylene is then removed under reduced pressure and the residue partitioned between brine and ethyl acetate. Ethyl acetate extracts are then washed with aqueous sodium bicarbonate and brine, dried over sodium sulfate, and concentrated. The crude product thusly obtained is chromatographed on silica gel, yielding pure lactone products.

Following the procedure of Example 5, each of the various 9-methylene-9-deoxy-PGF-type free acids described herein is transformed to a corresponding 1,11- or 1,15-lactone. Further, each of the various 9,11-dideoxy-9-methylene-PGF-type free acids described herein is transformed to a corresponding 9,11-dideoxy-9-methylene-PGF-type, 1,15-lacyone.

EXAMPLE 6

2-Decarboxy-2-hydroxymethyl-9-deoxy-9-methylene-PGF$_1$ (Formula XCII: Z$_1$, R$_8$, Y$_1$, M$_1$, L$_1$, and R$_7$ are as defined in Example 4).

Refer to Chart F.

750 mg. of 9-deoxy-9-methylene-PGF$_1$, methyl ester, dissolved in 50 ml. of diethyl ether are reacted with 500 mg. of lithium aluminum hydride at room temperature, with stirring. When the starting material is completely consumed (as indicated by thin layer chromatographic analysis) one ml. of water is cautiously added. Thereafter 0.8 ml. of 10 percent aqueous sodium hydroxide is added and the resulting mixture allowed to stir for 12 hr. Thereupon magnesium sulfate is added with stirring and the stirred mixture then filtered through magnesium sulfate and evaporated to a 700 mg. residue. Crystallization from ethyl acetate diethyl ether and hexane yields 493 mg. of pure title product. Melting point is 63°–64° C. Infrared absorptions are observed at 3400, 1460, 1370, 1120, 1070, 1060, 1020, 970, 880, 870, and 725 cm.$^{-1}$. NMR absorptions are observed at 5.7–5.30, 5.05–5.65, 4.25–3.35, and 2.90 δ. The mass spectrum exhibits a parent peak at 554.3993 and other peaks at 539, 483, 464, 449, 393, 267, 277, 199, and 173.

Following the procedure of Example 6, but employing each of the various formula XCI 9-deoxy or 9,11-dideoxy-9-methylene-PGF-type compounds of formula XCIV, there are prepared each of the various corresponding 2-decarboxy-2-hydroxymethyl-9-deoxy- or 9,11-dideoxy-9-methylene-PGF-type products.

EXAMPLE 7

2-Decarboxy-2-aminomethyl-9-deoxy-9-methylene-PGF$_1$ (Formula CIV: $Z_1$, $R_8$, $Y_1$, $M_1$, $L_1$, and $R_7$ are as defined in Example 4).

Refer to Chart G.

A. 9-deoxy-9-methylene-PGF$_1$, methyl ester is dissolved in one ml. of 95 percent ethanol. The resulting mixture is then transferred to a steel Parr bomb rinsed wih 2 one-half ml. aliquots of 95 percent ethanol and 200 mg. of ammonium chloride are added. Then the mixture is cooled in a dry ice acetone bath and ammonia is added until about 5 to 10 ml. has condensed. The bomb is then sealed and allowed to warm to room temperature. Thereafter the bomb is placed in an oven at 50° C. for 2 days cooled in a dry-ice acetone bath, and opened. Thereafter residual ammonia is evaporated with nitrogen and the product extracted with ethyl acetate, washed with water and saturated brine, dried over sodium sulfate, and evaporated to yield 9-deoxy-9-methylene-PGF$_1$ amide, formula CIII B. Lithium aluminum hydride (100 mg.) in 5 ml. of dry tetrahydrofuran under nitrogen is prepared. A solution of the reaction product of part A is then slowly added (being dissolved in a small amount of dry tetrahydrofuran). The resulting mixture is then stirred at room temperature for 48 hr. and thereafter one-tenth ml. ofwater is added while cooling the mixture in an ice bath. Thereafter 0.1 ml. of 15 percent sodium hydroxide and 0.3 ml. of water is added. The suspension is then filtered; dried over magnesium sulfate; washed with ethyl acetate; and evaporated to yield a residue of the title product.

EXAMPLE 8

9-Deoxy-9-methylene-PGF$_2$ (Formula LXXIV: $R_1$ is hydrogen, $Z_1$ is cis—CH=CH—(CH$_2$)$_3$—, $R_8$ is hydroxy, $Y_1$ is trans—CH=CH—, $R_3$ and $R_4$ of the $L_1$ moiety and $R_5$ of the $M_1$ moiety are all hydrogen and $R_7$ is n-butyl), or its methyl ester.

A. A stirred solution of 17 g. of N,S-dimethyl-S-phenylsulfoximine in 150 ml. of tetrahydrofuran is cooled to 0° C. and treated dropwise for 20 min. with 50 ml. of 2M methyl magnesium chloride in tetrahydrofuran. The reaction mixture is then stirred at 0° C. for an additional 15 min. and the resulting sulfoximine anion solution at 0° C. is then added dropwise over 45 min. to a well stirred solution of PGE$_2$, methyl ester, 11,15-bis-(trimethylsilyl ether) in 65 ml. of tetrahydrofuran. Stirred at −78° C. for an additional 2.5 hr., and then poured into saturated aqueous ammonium chloride, ice, and diethyl ether. The mixture is then extracted twice with brine, dried over magnesium sulfate, and concentrated.

B. The crude product obtained in part A is then dissolved in 900 ml. of tetrahydrofuran and treated with 140 ml. of water, 140 ml. of acetic acid, and an aluminum amalgam prepared from 30 g. of 20 mesh aluminum. The reaction temperature is maintained at 20°–25° C. After one hr. at ambient temperature several tablespoons of Celite are added and the reaction mixture after 10 min. of additional stirring is filtered through Celite and the salts washed with tetrahydrofuran. The filtrate is then concentrated to remove most of the tetrahydrofuran, then diluted with brine and extracted with ethyl acetate in hexane (4:6). Combined extracts are then washed with brine and 0.5M aqueous dibasic sodium phosphate. After drying over magnesium sulfate the extracts are evaporated under reduced pressure yielding 17.6 g. of crude product. This crude product is chromatographed on silica gel, packed with 30 percent ethyl acetate and hexane and eluted with 75 percent ethyl acetate in hexane. Accordingly, there are obtained 7.7 g. of pure title product. Infrared absorptions are observed at 3360, 3070, 1740, 1655, 1435, 1365, 1315, 1245, 1210, 1160, 1080, 1020, 970, and 875 cm.$^{-1}$. NMR absorptions are observed at 5.65–5.25, 4.90, 4.2–4.30, and 3.65 δ. The mass spectrum exhibits peaks at 328, 315, 375, 247, 243, and 205.

C. The title methyl ester prepared in part B above is then transformed to the corresponding free acid by reacting 200 mg. of the reaction product of part B above in 5 ml. of methanol with 3 ml. of 3N potassium hydroxide. This mixture is stirred under nitrogen atmosphere for 1.5 hr. at ambient temperature and thereafter poured into a mixture of brine and ice and acidified with 2M sodium bisulfate. This mixture is then extracted with ethyl acetate and the ethyl acetate extracts washed with brine and dried over sodium sulfate and evaporated to yield 350 mg. of a residue as a crude oil. Chromatographic purification on silica gel yields pure title product (210 mg.). Infrared absorptions are observed at 3400, 2950, 2650, 1720, 1660, 1240, 1075, 970, and 885 cm.$^{-1}$. NMR absorptions are observed at 5.8, 5.7–5.20, 5.05–4.75, and 4.35–3.5 δ. The mass spectrum exhibits peaks at 332, 314, 303, 205, 187, 177, 161, 145, and 135.

EXAMPLE 9

9-Deoxy-9-methylene-16,16-dimethyl-PGF$_2$ (Formula LXXIV: $R_1$ is hydrogen, $Z_1$ is cis—CH=•CH—(CH$_2$)$_3$—, $R_8$ is hydroxy, $Y_1$ is trans—CH=CH—, $R_3$ and $R_4$ of the $L_1$ moiety are methyl and $R_5$ of the $M_1$ moiety is hydrogen, and $R_7$ is n-butyl) or its methyl ester.

Refer to Chart D.

A solution of 700 mg. of N,S-dimethyl-S-phenylsulfoximine in 10 ml. of tetrahydrofuran is cooled to 0° C. and treated with 2 ml. of 2M methylmagnesium chloride and tetrahydrofuran. After 20 min. at 0° C. the sulfoximine anion solution is then cooled to −78° C. and the solution of 500 mg. of 16,16-dimethyl-PGE$_2$, methyl ester, 11,15-bis-(trimethylsilyl ether) in 3 ml. of tetrahydrofuran are added dropwise. The resulting mixture is stirred at −78° C. for 1.5 hr., and then poured into cold aqueous ammonium chloride. The resulting mixture is then extracted with diethyl ether and the combined extracts are washed with brine, dried over sodium sulfate, and concentrated under reduced pressure to a residue. This crude residue is then dissolved in 50 ml. of methanol and treated with 25 ml. of a 2.5 percent aqueous citric acid solution. After 30 min. at ambient temperature the reaction mixture is diluted with brine and extracted with ethyl acetate. Ethyl acetate extracts are then washed with brine and dried over sodium sulfate and evaporated to a residue.

B. The crude residue of part A is then dissolved in a mixture of 20 ml. tetrahydrofuran, 3.5 ml. of water, and 3.5 ml. of acetic acid treated with aluminum malgum, prepared from 800 mg. of 20 mesh aluminum. The reaction mixture is then stirred vigorously at 20°–25° C. for one hr. and thereafter filtered through Celite and solids therefrom washed with fresh tetrahydrofuran. The combined filtrate is then diluted with excess aqueous sodium bicarbonate and concentrated under reduced pressure to a residue. This residue is then extracted with ethyl acetate and the combined organic extracts washed with brine, dried over sodium sulfate, and evaporated to a residue. The second residue is then chromatographed on silica gel, packed with 20 percent ethyl acetate and hexane. Eluting with 50 percent ethyl acetate and hexane pure title methyl ester is obtained (69 mg.). Infrared absorptions are observed at 3500, 3140, 1750, 1670, 1240, 1160, 1080, 1020, 1000, 975, and 885 cm.$^{-1}$. NMR absorptions are observed at 5.75–5.20, 4.90, 3.64, 3.05, 0.85, and 0.82 δ.

To a solution of the title methyl ester prepared above (69 mg.) in 5 ml. of methanol is added 2.5 ml. of 3N aqueous potassium hydroxide. The resulting mixture is then stirred for 2 hr. at ambient temperature and thereafter diluted with 100 ml. of water and extracted with diethyl ether. The aqueous layer is then acidified with cold 1M aqueous potassium bisulfate and extracted thoroughly with ethyl acetate. The combined extract is then washed with brine, dried over sodium sulfate, and concentrated under reduced pressure. This crude residue is then chromatographed on acid washed silica gel packed with 40 percent ethyl acetate in hexane. Eluting with 80 percent acetate and hexane 63 mg. of pure title free acid are obtained. The mass spectrum exhibits parent peak at 594 and 5879.3706 and other peaks at 504, 495, 489, 405, and 243.

EXAMPLE 10

17-Phenyl-18,19,20-trinor-9-deoxy-9-methylene-PGF$_2$ (Formula LXXIV: R$_1$ is methyl, Z$_1$ is cis—CH=•CH—(CH$_2$)$_3$—, R$_8$ is hydrogen, Y$_1$ is trans—CH=•CH—, R$_3$ and R$_4$ of the L$_1$ moiety and R$_5$ of the M$_1$ moiety are all hydrogen, and R$_7$ is benzyl) or its methyl ester.

Refer to Chart D.

A. 17-phenyl-18,19,20-trinor-PGE$_2$, methyl ester, 11,15-bis(trimethylsilyl ether), 2.1 g., and 10 ml. of tetrahydrofuran are reacted following the procedure of Example 9, part A.

B. The reaction product of part A above is reacted with 50 ml. of 2.5 percent aqueous citric acid, 105 ml. of tetrahydrofuran, 16 ml. of water, 16 ml. of acetic acid, and an aluminum amalgam prepared from 3.5 g. of 20 mesh aluminum, yielding 482 g. of title methyl ester.

C. The title methyl ester is then transformed to the corresponding free acid following the procedure of Example 9, part C, yielding crystalline title product. Melting point is 62°–64° C. Infrared absorptions are observed at 3400, 3100, 3050, 2965, 2650, 1720, 1665, 1610, 1500, 1240, 1075, 1050, 970, 890, 755, and 700 cm.$^{-1}$. NMR absorptions are observed at 7.35–7.10, 5.85–5.20, 4.90, and 4.25–3.50 δ. The mass spectrum exhibits a parent peak at 600.3554 and other peaks at 585, 570, 495, 420, 405, 315, 311, 233, and 91.

EXAMPLE 11

15-Methyl-9-deoxy-9-methylene-PGF$_2$ (Formula LXXIV: R$_1$ is hydrogen, Z$_1$ is cis—CH=CH—(CH$_2$)$_3$—, R$_8$ is hydroxy, Y$_1$ is trans—CH=CH—, R$_3$ and R$_4$ of the L$_1$ moiety are hydrogen, R$_5$ of the M$_1$ moiety is methyl, and R$_7$ is n-butyl) or its methyl ester, or the 15-epimers thereof.

A. 9-Deoxy-9-methylene-PGF$_2$, methyl ester (Example 8, 450 mg.) 323 mg. of 2,3-dichloro-5,6-dicyano-benzoquinone and 20 ml. of dioxane are stirred under a nitrogen atmosphere at room temperature for 24 hr. and thereafter the resulting mixture is diluted with dichloromethane filtered through Celite and the filter cake washed with dichloromethane. Concentration under reduced pressure and chromatography of the residue on 70 g. of silica gel yields 355 mg. of the 15-keto product corresponding to the Example 8 starting material.

B. The reaction product of part A above (355 mg.) 10 ml. of tetrahydrofuran, 4 ml. of hexamethyldisilazane and one ml. of trimethylchlorosilane stirred at ambient temperature for 4 hr. and thereafter the solvents are removed under reduced pressure. To the resulting residue xylene is added and the resulting mixture filtered through Celite. Xylene is then removed under reduced pressure yielding th 11-trimethylsilyl ether of the starting material.

C. The crude product from part B above is dissolved in 40 ml. of benzene and thereafter with stirring, at 15° C. trimethylaluminum is added over a period of about 2 min. Stirring continues for an additional 25 min. and thereafter 45 ml. of saturated aqueous ammonium chloride is added. The resulting mixture is then washed with brine and extracted with diethyl ether. The ethereal extracts are then washed with brine, dried over magnesium sulfate and evaporated under reduced pressure to yield a residue of crude (15RS)-15-methyl products.

D. The crude reaction product of part C above in 35 ml. of methanol is reacted with 17 ml. of 2 percent aqueous citric acid at room temperature, with stirring for 30 min. The resulting mixture is then poured into brine and extracted with ethyl acetate. The organic extracts are then washed with water, sodium bicarbonate, brine, and dried over sodium sulfate. Concentration under reduced pressure yields 400 mg. of (15RS)-15-methyl-9-deoxy-9-methylene-PGF$_2$, methyl ester. Chromatographing the crude produce on 75 g. of neutral silica gel packed with 5 percent acetone in dichloromethane and eluting with 20 percent acetone in dichloromethane yields 132 mg. of pure (R) methyl ester and 150 mg. of pure (15S) methyl ester.

E. Each of the pure methyl esters of part B above is transformed to the corresponding free acid by reaction with 10 percent aqueous potassium hydroxide in methanol. Accordingly, 132 mg. of the 15-epi title methyl ester is transformed to 129 mg. of the 15-epi title free acid and 130 mg. of the (15S) methyl ester is transformed to 120 mg. of the title free acid. For each of these free acids infrared absorptions are observed at 3400, 3100, 2650, 1715, 1655, 1240, 1070, 970, and 885 cm.$^{-1}$. NMR absorptions are observed at 5.80, 5.3, 4.95, 4.85, 4.35–3.60, and 1.25 δ.

Following the procedure described in the preceeding Examples each of the various 9-deoxy-9-methylene-PGF compounds described above is prepared.

I claim:

1. A prostaglandin analog of the formula:

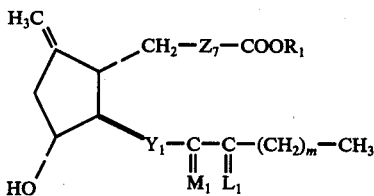

wherein $Y_1$ is trans—CH=CH—, —C≡C—, or —CH$_2$CH$_2$—; wherein $M_1$ is

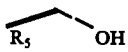

or

wherein $R_5$ is hydrogen or methyl; wherein $L_1$ is

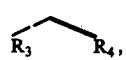

or a mixture of

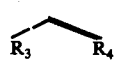

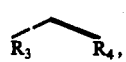

wherein $R_3$ and $R_4$ are hydrogen, methyl, or fluoro, being the same or different, with the proviso that one of $R_3$ and $R_4$ is fluoro only when the other is hydrogen or fluoro;
wherein $Z_7$ is
1. cis—CH=CH—CH$_2$—(CH$_2$)$_g$—CH$_2$—,
2. cis—CH=CH—CH$_2$—(CH$_2$)$_g$—CF$_2$—,
3. cis—CH$_2$—CH=CH—(CH$_2$)$_g$—CH$_2$—,
4. —(CH$_2$)$_3$—(CH$_2$)$_g$—CH$_2$—,
5. —(CH$_2$)$_3$—(CH$_2$)$_g$—CF$_2$—,
6. —CH$_2$—O—CH$_2$—(CH$_2$)$_g$—CH$_2$—,
7. —C≡C—CH$_2$—(CH$_2$)$_g$—CH$_2$—, or
—CH$_2$—C≡C—(CH$_2$)$_g$—CH$_2$—,
wherein g is one, 2, or 3;
wherein m is one to 5, inclusive; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A prostaglandin analog according to claim 1, wherein $Y_1$ is —CH$_2$CH$_2$—.

3. A prostaglandin analog according to claim 2, wherein $Z_7$ is cis—CH=CH—CH$_2$—(CH$_2$)$_g$—CF$_2$—.

4. 9-Deoxy-9-methylene-2,2-difluoro-13,14-dihydro-PGF$_2$, a prostaglandin analog according to claim 3.

5. A prostaglandin analog according to claim 2, wherein $Z_7$ is —(CH$_2$)$_3$—(CH$_2$)$_g$—CF$_2$—.

6. 9-Deoxy-9-methylene-2,2-difluoro-13,14dihydro-PGF$_1$, a prostaglandin analog according to claim 5.

7. A prostaglandin analog according to claim 2, wherein $Z_1$ is cis—CH$_2$—CH=CH—(CH$_2$)$_g$—CH$_2$13.

8. 9-Deoxy-9-methylene-cis-4,5-didehydro-13,14-dihydro-PGF$_1$, a prostaglandin analog according to claim 7.

9. A prostaglandin analog according to claim 2, wherein $Z_7$ is —CH$_2$—O—CH$_2$—(CH$_2$)$_g$—CH$_2$—.

10. 9-Deoxy-9-methylene-5-oxa-13,14-dihydro-PGF$_1$, a prostaglandin analog according to claim 9.

11. A prostaglandin analog according to claim 2, wherein $Z_7$ is —C≡C—CH$_2$—(CH$_2$)$_g$—CH$_2$—.

12. 9-Deoxy-9-methylene-5,6-didehydro-13,14-dihydro-PGF$_2$, a prostaglandin analog according to claim 11.

13. A prostaglandin analog according to claim 2, wherein $Z_7$ is —CH$_2$—C≡C—(CH$_2$)$_g$—CH$_2$—.

14. 9-Deoxy-9-methylene-4,4,5,5-tetradehydro-13,14-dihydro-PGF$_1$, a prostaglandin analog according to claim 13.

15. A prostaglandin analog according to claim 2, wherein $Z_7$ is —(CH$_2$)$_3$—(CH$_2$)$_g$—CH$_2$—.

16. A prostaglandin analog according to claim 15, wherein $M_1$ is

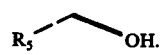

17. 9-Deoxy-9-methylene-15-epi-13,14-dihydro-PGF$_1$, a prostaglandin analog according to claim 16.

18. A prostaglandin analog according to claim 15, wherein $M_1$ is

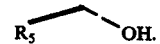

19. A prostaglandin analog according to claim 18, wherein m is 3.

20. A prostaglandin analog according to claim 19, wherein g is 3.

21. 9-Deoxy-9-methylene-2a,2b-dihomo-15-methyl-13,14-dihydro-PGF$_1$, a prostaglandin analog according to claim 20.

22. 9-Deoxy-9-methylene-2a,2b-dihomo-13,14-dihydro-PGF$_1$, a prostaglandin analog according to claim 20.

23. A prostaglandin analog according to claim 19, wherein g is 1.

24. A prostaglandin analog according to claim 23, wherein at least one of $R_3$ and $R_4$ is methyl.

25. A prostaglandin analog according to claim 24, wherein $R_3$ and $R_4$ are both methyl.

26. 9-Deoxy-9-methylene-16,16-dimethyl-13,14-dihydro-PGF$_1$, a prostaglandin analog according to claim 25.

27. A prostaglandin analog according to claim 23, wherein at least one or $R_3$ and $R_4$ is fluoro.

28. A prostaglandin analog according to claim 27, wherein $R_3$ and $R_4$ ar both fluoro.

29. 9-Deoxy-9-methylene-16,16-difluoro-13,14-dihydro-PGF$_1$, a prostaglandin analog according to claim 28.

30. A prostaglandin analog according to claim 23, wherein $R_3$ and $R_4$ are both hydrogen.

31. A prostaglandin analog according to claim 30, wherein $R_5$ is methyl.

32. 9-Deoxy-9-methylene-15-methyl-13,14-dihydro-PGF$_1$, a prostaglandin analog according to claim 31.

33. A prostaglandin analog according to claim 30, wherein R$_5$ is hydrogen.

34. 9-Deoxy-9-methylene 13,14dihydro-PGF$_1$, a prostaglandin analog according to claim 33.

35. A prostaglandin analog according to claim 2, wherein Z$_7$ is cis—CH═CH—CH$_2$—(CH$_2$)$_g$—CH$_2$—.

36. A prostaglandin analog according to claim 35, wherein M$_1$ is

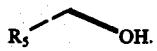

37. A prostaglandin analog according to claim 36, wherein m is 3.

38. A prostaglandin analog according to claim 37, wherein g is 3.

39. 9-Deoxy-9-methylene-2a,2b-dihomo-15-epi-15-methyl-13,14-dihydro-PGF$_2$, a prostaglandin analog according to claim 38.

40. 9-Deoxy-9-methylene-2a,2b-dihomo-15-epi-13,14-dihydro-PGF$_2$, a prostaglandin analog according to claim 38.

41. A prostaglandin analog according to claim 37, wherein g is 1.

42. A prostaglandin analog according to claim 41, wherein at least one of R$_3$ and R$_4$ is methyl.

43. 9-Deoxy-9-methylene-15-epi-16,16-dimethyl-13,14-dihydro-PGF$_2$, a prostaglandin analog according to claim 42.

44. A prostaglandin analog according to claim 41, wherein at least one of R$_3$ and R$_4$ is fluoro.

45. 9-Deoxy-9-methylene-15-epi-16,16-difluoro-13,14-dihydro-PGF$_2$, a prostaglandin analog according to claim 44.

46. A prostaglandin analog according to claim 41, wherein R$_3$ and R$_4$ are both hydrogen.

47. 9-Deoxy-9-methylene-15-epi-15-methyl-13,14-dihydro-PGF$_2$, a prostaglandin analog according to claim 46.

48. A prostaglandin analog according to claim 35, wherein M$_1$ is

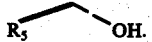

49. A prostaglandin analog according to claim 48, wherein m is 3.

50. A prostaglandin analog according to claim 49, wherein g is 3.

51. A prostaglandin analog according to claim 50, wherein at least one of R$_3$ and R$_4$ is methyl.

52. 9-Deoxy-9-methylene-2a,2b-dihomo-16,16-dimethyl-13,14-dihydro-PGF$_2$, a prostaglandin analog according to claim 51.

53. A prostaglandin analog according to claim 50, wherein at least one of R$_3$ and R$_4$ is fluoro.

54. 9-Deoxy-9-methylene-2a,2b-dihomo-16,16-difluoro-13,14-dihydro-PGF$_2$, a prostaglandin analog according to claim 53.

55. A prostaglandin analog according to claim 50, wherein R$_3$ and R$_4$ are both hydrogen.

56. 9-Deoxy-9-methylene-2a,2b-dihomo-15-methyl-13,14-dihydro-PGF$_2$, a prostaglandin analog according to claim 55.

57. A prostaglandin analog according to claim 49, wherein g is 1.

58. A prostaglandin analog according to to claim 57, wherein at leat one of R$_3$ and R$_4$ is methyl.

59. A prostaglandin analog according to claim 58, wherein R$_3$ and R$_4$ are both methyl.

60. 9-Deoxy-9-methylene-16,16-dimethyl-13,14-dihydro-PGF$_2$, tris-(hydroxymethyl)aminomethane salt, a prostaglandin analog according to claim 59.

61. 9-Deoxy-9-methylene-16,16-dimethyl-13,14-dihydro-PGF$_2$, methyl ester, a prostaglandin analog according to claim 59.

62. 9-Deoxy-9-methylene-16,16-dimethyl-13,14-dihydro-PGF$_2$, a prostaglandin analog according to claim 59.

63. A prostaglandin analog according to claim 57, wherein at least one of R$_3$ and R$_4$ is fluoro.

64. A prostaglandin analog according to claim 63, wherein R$_3$ and R$_4$ are both fluoro.

65. A prostaglandin analog according to claim 64, wherein R$_5$ is methyl.

66. 9-Deoxy-9-methylene-15-methyl-16,16-difluoro-13,14-dihydro-PGF$_2$, a prostaglandin analog according to claim 65.

67. A prostaglandin analog according to claim 64, wherein R$_5$ is hydrogen.

68. 9-Deoxy-9-methylene-16,16-difluoro-13,14-dihydro-PGF$_2$, a prostaglandin analog according to claim 67.

69. A prostaglandin analog according to claim 57, wherein R$_3$ and R$_4$ are both hydrogen.

70. A prostaglandin analog according to claim 69, wherein R$_5$ is methyl.

71. 9-Deoxy-9-methylene-15-methyl-13,14-dihydro-PGF$_2$, tris-(hydroxymethyl)aminomethane salt, a prostaglandin analog according to claim 70.

72. 9-Deoxy-9-methylene-15-methyl-13,14-dihydro-PGF$_2$, methyl ester, a prostaglandin analog according to claim 70.

73. 9-Deoxy-9-methylene-15-methyl-13,14-dihydro-PGF$_2$, a prostaglandin analog according to claim 70.

74. A prostaglandin analog according to claim 69, wherein R$_5$ is hydrogen.

75. 9-Deoxy-9-methylene-13,14-dihydro-PGF$_2$, methyl ester, a prostaglandin analog according to claim 74.

76. 9-Deoxy-9-methylene-13,14-dihydro-PGF$_2$, a prostaglandin analog according to claim 74.

77. A prostaglandin analog according to claim 1, wherein Y$_1$ is —C≡C—.

78. A prostaglandin analog according to claim 77, wherein Z$_7$ is cis—CH═CH—CH$_2$—(CH$_2$)$_g$—CF$_2$—.

79. 9-Deoxy-9-methylene-2,2-difluoro-13,14-didehydro-PGF$_2$, a prostaglandin analog according to claim 78.

80. A prostaglandin analog according to claim 77, wherein Z$_7$ is —(CH$_2$)$_3$—(CH$_2$)$_g$—CF$_2$—.

81. 9-Deoxy-9-methylene-2,2-difluoro-13,14-didehydro-PGF$_1$, a prostaglandin analog according to claim 80.

82. A prostaglandin analog according to claim 77, wherein Z$_7$ is cis—CH$_2$—CH═CH—(CH$_2$)$_g$—CH$_2$—.

83. 9-Deoxy-9-methylene-cis-4,5-didehydro-13,14-didehydro-PGF$_1$, a prostaglandin analog according to claim 82.

84. A prostaglandin analog according to claim 77, wherein Z$_7$ is —CH$_2$—O—CH$_2$—(CH$_2$)$_g$—CH$_2$—.

85. 9-Deoxy-9-methylene-5-oxa-13,14-didehydro-PGF₁, a prostaglandin analog according to claim 84.

86. A prostalgandin analog according to claim 77, wherein Z₇ is —C≡C—CH₂—(CH₂)ᵍ—CH₂—.

87. 9-Deoxy-9-methylene-5,6,13,14-tetradehydro-PGF₂, a prostaglandin analog according to claim 86.

88. A prostaglandin analog according to claim 77, wherein Z₇ is —CH₂—C≡C—(CH₂)ᵍ—CH₂—.

89. 9-Deoxy-9-methylene-4,4,5,5,13,14-hexadehydro-PGF₁, a prostaglandin analog according to claim 88.

90. A prostaglandin analog according to claim 77, wherein Z₇ is —(CH₂)₃—(CH₂)ᵍ—CH₂—.

91. A prostaglandin analog according to claim 90, wherein M₁ is

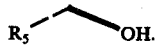

92. 9-Deoxy-9-methylene-15-epi-13,14-didehydro-PGF₁, a prostaglandin analog according to claim 91.

93. A prostaglandin analog according to claim 90, wherein M₁ is

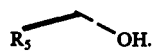

94. A prostaglandin analog according to claim 93, wherein m is 3.

95. A prostaglandin analog according to claim 94, wherein g is 3.

96. 9-Deoxy-9-methylene-2a,2b-dihomo-15-methyl-13,14-didehydro-PGF₁, a prostaglandin analog according to claim 95.

97. 9-Deoxy-9-methylene-2a,2b-dihomo-13,14-didehydro-PGF₁, a prostaglandin analog according to claim 95.

98. A prostaglandin analog according to claim 94, wherein g is 1.

99. A prostaglandin analog according to claim 98, wherein at least one of R₃ and R₄ is methyl.

100. A prostaglandin analog according to claim 99, wherein R₃ and R₄ are both methyl.

101. 9-Deoxy-9-methylene-16,16-dimethyl-13,14-didehydro-PGF₁, a prostaglandin analog according to claim 100.

102. A prostaglandin analog according to claim 98, wherein at least one of R₃ and R₄ is fluoro.

103. A prostaglandin analog according to claim 102, wherein R₃ and R₄ are both fluoro.

104. 9-Deoxy-9-methylene-16,16-difluoro-13,14-didehydro-PGF₁, a prostaglandin analog according to claim 103.

105. A prostaglandin analog according to claim 98, wherein R₃ and R₄ are both hydrogen.

106. A prostaglandin analog according to claim 105, wherein R₅ is methyl.

107. 9-Deoxy-9-methylene-15-methyl-13,14-didehydro-PGF₁, a prostaglandin analog according to claim 106.

108. A prostaglandin analog according to claim 105, wherein R₅ is hydrogen.

109. 9-Deoxy-9-methylene-13,14-didehydro-PGF₁, a prostaglandin analog according to claim 108.

110. A prostaglandin analog according to claim 77, wherein Z₇ is cis—CH=CH—CH₂—(CH₂)ᵍ—CH₂—.

111. A prostaglandin analog according to claim 110, wherein M₁ is

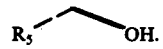

112. A prostaglandin analog according to claim 111, wherein m is 3.

113. A prostaglandin analog according to claim 112, wherein g is 3.

114. 9-Deoxy-9-methylene-2a,2b-dihomo-15-epi-15-methyl-13,14-didehydro-PGF₂, a prostaglandin analog according to claim 113.

115. 9-Deoxy-9-methylene-2a,2b-dihomo-15-epi-13,14-didehydro-PGF₂, a prostaglandin analog according to claim 113.

116. A prostaglandin analog according to claim 112, wherein g is 1.

117. A prostaglandin analog according to claim 116, wherein at least one of R₃ and R₄ is methyl.

118. 9-Deoxy-9-methylene-15-epi-16,16-dimethyl-13,14-didehydro-PGF₂, a prostaglandin analog according to claim 117.

119. A prostaglandin analog according to claim 116, wherein at least one of R₃ and R₄ is fluoro.

120. 9-Deoxy-9-methylene-15-epi-16,16-difluoro-13,14-didehydro-PGF₂, a prostaglandin analog according to claim 119.

121. A prostaglandin analog according to claim 116, wherein R₃ and R₄ are both hydrogen.

122. 9-Deoxy-9-methylene-15-epi-15-methyl-13,14-didehydro-PGF₂, a prostaglandin analog according to claim 121.

123. A prostaglandin analog according to claim 110, wherein M₁ is

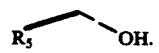

124. A prostaglandin analog according to claim 123, wherein m is 3.

125. A prostaglandin analog according to claim 124, wherein g is 3.

126. A prostaglandin analog according to claim 125, wherein at least one or R₃ and R₄ is methyl.

127. 9-Deoxy-9-methylene-2a,2b-dihomo-16,16-dimethyl-13,14-didehydro-PGF₂, a prostaglandin analog according to claim 126.

128. A prostaglandin analog according to claim 125, wherein at least one or R₃ and R₄ is fluoro.

129. 9-Deoxy-9-methylene-2a,2b-dihomo-16,16-difluoro-13,14-didehydro-PGF₂, a prostaglandin analog according to claim 128.

130. A prostaglandin analog according to claim 125, wherein R₃ and R₄ are both hydrogen.

131. 9-Deoxy-9-methylene-2a,2b-dihomo-15-methyl-13,14-didehydro-PGF₂, a prostaglandin analog according to claim 130.

132. A prostaglandin analog according to claim 124, wherein g is 1.

133. A prostaglandin analog according to claim 132, wherein at least one of R₃ and R₄ is methyl.

134. A prostaglandin analog according to claim 133, wherein R₃ and R₄ are both methyl.

135. 9-Deoxy-9-methylene-16,16-dimethyl-13,14-didehydro-PGF₂, tris(hydroxymethyl)aminomethane salt, a prostaglandin analog according to claim 134.

136. 9-Deoxy-9-methylene-16,16-dimethyl-13,14-didehydro-PGF$_2$, methyl ester, a prostaglandin analog according to claim 134.

137. 9-Deoxy-9-methylene-16,16-dimethyl-13,14-didehydro-PGF$_2$, a prostaglandin analog according to claim 134.

138. A prostaglandin analog according to claim 132, wherein at least one of R$_3$ and R$_4$ is fluoro.

139. A prostaglandin analog according to claim 138, wherein R$_3$ and R$_4$ are both fluoro.

140. A prostaglandin analog according to claim 139, wherein R$_5$ is methyl.

141. 9-Deoxy-9-methylene-15-methyl-16,16-difluoro-13,14-didehydro-PGF$_2$, a prostaglandin analog according to claim 140.

142. A prostaglandin analog according to claim 139, wherein R$_5$ is hydrogen.

143. 9-Deoxy-9-methylene-16,16-difluoro-13,14-didehydro-PGF$_2$, a prostaglandin analog according to claim 142.

144. A prostaglandin analog according to claim 132, wherein R$_3$ and R$_4$ are both hydrogen.

145. A prostaglandin analog according to claim 144, wherein R$_5$ is methyl.

146. 9-Deoxy-9-methylene-15-methyl-13,14-didehydro-PGF$_2$, tris(hydroxymethyl)aminomethane salt, a prostaglandin analog according to claim 145.

147. 9-Deoxy-9-methylene-15-methyl-13,14-didehydro-PGF$_2$, methyl ester, a prostaglandin analog according to claim 145.

148. 9-Deoxy-9-methylene-15-methyl-13,14-didehydro-PGF$_2$, a prostaglandin analog according to claim 145.

149. A prostaglandin analog according to claim 144, wherein R$_5$ is hydrogen.

150. 9-Deoxy-9-methylene-13,14-didehydro-PGF$_2$, methyl ester, a prostaglandin analog according to claim 149.

151. 9-Deoxy-9-methylene-13,14-didehydro-PGF$_2$, a prostaglandin analog according to claim 149.

152. A prostaglandin analog according to claim 1, wherein Y$_1$ is trans—CH=CH—.

153. A prostaglandin analog according to claim 152, wherein Z$_7$ is cis—CH=CH—CH$_2$—(CH$_2$)$_g$—CF$_2$—.

154. 9-Deoxy-9-methylene-2,2-difluoro-PGF$_2$, a prostaglandin analog according to claim 153.

155. A prostaglandin analog according to claim 152, wherein Z$_7$ is —(CH$_2$)$_3$—(CH$_2$)$_g$—CF$_2$—.

156. 9-Deoxy-9-methylene-2,2-difluoro-PGF$_1$, a prostaglandin analog according to claim 155.

157. A prostaglandin analog according to claim 152, wherein Z$_1$ is cis—CH$_2$—CH=CH—(CH$_2$)$_g$—CH$_2$—.

158. 9-Deoxy-9-methylene-cis-4,5-didehydro-PGF$_1$, a prostaglandin analog according to claim 157.

159. A prostaglandin analog according to claim 152, wherein Z$_7$ is —CH$_2$—O—CH$_2$—(CH$_2$)$_g$—CH$_2$—.

160. 9-Deoxy-9-methylene-5-oxa-PGF$_1$, a prostaglandin analog according to claim 159.

161. A prostaglandin analog according to claim 152, wherein Z$_7$ is —C≡C—CH$_2$—(CH$_2$)$_g$—CH$_2$—.

162. 9-Deoxy-9-methylene-5,6-didehydro-PGF$_2$, a prostaglandin analog according to claim 161.

163. A prostaglandin analog according to claim 152, wherein Z$_7$ is —CH$_2$—C≡C—(CH$_2$)$_g$—CH$_2$—.

164. 9-Deoxy-9-methylene-4,4,5,5-tetrahydro-PGF$_1$, a prostaglandin analog according to claim 163.

165. A prostaglandin analog according to claim 152, wherein Z$_7$ is —(CH$_2$)$_3$—(CH$_2$)$_g$—CH$_2$—.

166. A prostaglandin analog according to claim 165, wherein M$_1$ is

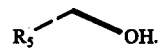

167. 9-Deoxy-9-methylene-15-epi-PGF$_1$, a prostaglandin analog according to claim 166.

168. A prostaglandin analog according to claim 165, wherein M$_1$ is

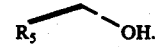

169. A prostaglandin analog according to claim 168, wherein m is 3.

170. A prostaglandin analog according to claim 169, wherein g is 3.

171. 9-Deoxy-9-methylene-2a,2b-dihomo-15-methyl-PGF$_1$, a prostaglandin analog according to claim 170.

172. 9-Deoxy-9-methylene-2a,2b-dihomo-PGF$_1$, a prostaglandin analog according to claim 170.

173. A prostaglandin analog according to claim 169, wherein g is 1.

174. A prostaglandin analog according to claim 173, wherein at least one of R$_3$ and R$_4$ is methyl.

175. A prostaglandin analog according to claim 174, wherein R$_3$ and R$_4$ are both methyl.

176. 9-Deoxy-9-methylene-16,16-dimethyl-PGF$_1$, a prostaglandin analog according to claim 175.

177. A prostaglandin analog according to claim 173, wherein at least one of R$_3$ and R$_4$ is fluoro.

178. A prostaglandin analog according to claim 177, wherein R$_3$ and R$_4$ are both fluoro.

179. 9-Deoxy-9-methylene-16,16-difluoro-PGF$_1$, a prostaglandin analog according to claim 178.

180. A prostaglandin analog according to claim 173, wherein R$_3$ and R$_4$ are both hydrogen.

181. A prostaglandin analog according to claim 180, wherein R$_5$ is methyl.

182. 9-Deoxy-9-methylene-15-methyl-PGF$_1$, a prostaglandin analog according to claim 181.

183. A prostaglandin analog according to claim 180, wherein R$_5$ is hydrogen.

184. 9-Deoxy-9-methylene-PGF$_1$, a prostaglandin analog according to claim 183.

185. A prostaglandin analog according to claim 152, wherein Z$_7$ is cis—CH=CH—CH$_2$—(CH$_2$)$_g$—CH$_2$—.

186. A prostaglandin analog according to claim 185, wherein M$_1$ is

187. A prostaglandin analog according to claim 186, wherein m is 3.

188. A prostaglandin analog according to claim 187, wherein g is 3.

189. 9-Deoxy-9-methylene-2a,2b-dihomo-15-epi-15-methyl-PGF$_2$, a prostaglandin analog according to claim 188.

190. 9-Deoxy-9-methylene-2a,2b-dihomo-15-epi-PGF$_2$, a prostaglandin analog according to claim 188.

191. A prostaglandin analog according to claim 187, wherein g is 1.

192. A prostaglandin analog according to claim 191, wherein at least one of $R_3$ and $R_4$ is methyl.

193. 9-Deoxy-9-methylene-15-epi-16,16-dimethyl-$PGF_2$, a prostaglandin analog according to claim 192.

194. A prostaglandin analog according to claim 191, wherein at least one of $R_3$ and $R_4$ is fluoro.

195. 9-Deoxy-9-methylene-15-epi-16,16-difluoro-$PGF_2$, a prostaglandin analog according to claim 194.

196. A prostaglandin analog according to claim 191, wherein $R_3$ and $R_4$ are both hydrogen.

197. 9-Deoxy-9-methylene-15-epi-15-methyl-$PGF_2$, a prostaglandin analog according to claim 196.

198. A prostaglandin analog according to claim 185, wherein $M_1$ is

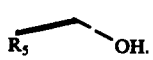

199. A prostaglandin analog according to claim 198, wherein $m$ is 3.

200. A prostaglandin analog according to claim 199, wherein $g$ is 3.

201. A prostaglandin analog according to claim 200, wherein at least one of $R_3$ and $R_4$ is methyl.

202. 9-Deoxy-9-methylene-2a,2b-dihomo-16,16-dimethyl-$PGF_2$, a prostaglandin analog according to claim 201.

203. A prostaglandin analog according to claim 200, wherein at least one or $R_3$ and $R_4$ is fluoro.

204. 9-Deoxy-9-methylene-2a,2b-dihomo-16,16-difluoro-$PGF_2$, a prostaglandin analog according to claim 201.

205. A prostaglandin analog according to claim 200, wherein $R_3$ and $R_4$ are both hydrogen.

206. 9-Deoxy-9-methylene-2a,2b-dihomo-15-methyl-$PGF_2$, a prostaglandin analog according to claim 205.

207. A prostaglandin analog according to claim 199, wherein $g$ is 1.

208. A prostaglandin analog according to claim 207, wherein at least one of $R_3$ and $R_4$ is methyl.

209. A prostaglandin analog according to claim 208, wherein $R_3$ and $R_4$ are both methyl.

210. 9-Deoxy-9-methylene-16,16-dimethyl-$PGF_2$, tris(hydroxymethyl)aminomethane salt, a prostaglandin analog according to claim 209.

211. 9-Deoxy-9-methylene-16,16-dimethyl-$PGF_2$, methyl ester, a prostaglandin analog according to claim 209.

212. 9-Deoxy-9-methylene-16,16-dimethyl-$PGF_2$, a prostaglandin analog according to claim 209.

213. A prostaglandin analog according to claim 207, wherein at least one of $R_3$ and $R_4$ is fluoro.

214. A prostaglandin analog according to claim 213, wherein $R_3$ and $R_4$ are both fluoro.

215. A prostaglandin analog according to claim 214, wherein $R_5$ is methyl.

216. 9-Deoxy-9-methylene-15-methyl-16,16-difluoro-$PGF_2$, a prostaglandin analog according to claim 215.

217. A prostaglandin analog according to claim 214, wherein $R_5$ is hydrogen.

218. 9-Deoxy-9-methylene-16,16-difluoro-$PGF_2$, a prostaglandin analog according to claim 217.

219. A prostaglandin analog according to claim 207, wherein $R_3$ and $R_4$ are both hydrogen.

220. A prostaglandin analog according to claim 219, wherein $R_5$ is methyl.

221. 9-Deoxy-9-methylene-15-methyl-$PGF_2$, tris(hydroxymethyl)aminomethane salt, a prostaglandin analog according to claim 220.

222. 9-Deoxy-9-methylene-15-methyl-$PGF_2$, methyl ester, a prostaglandin analog according to claim 220.

223. 9-Deoxy-9-methylene-15-methyl-$PGF_2$, a prostaglandin analog according to claim 220.

224. A prostaglandin analog according to claim 219, wherein $R_5$ is hydrogen.

225. 9-Deoxy-9-methylene-$PGF_2$, methyl ester, a prostaglandin analog according to claim 224.

226. 9-Deoxy-9-methylene-$PGF_2$, a prostaglandin analog according to claim 224.

* * * * *

UNITED STATES PATENT OFFICE
CERTIFICATE OF CORRECTION

Patent No. 4,060,534　　　　　　　　Dated 29 November 1977

Inventor(s) Gordon L. Bundy

It is certified that error appears in the above-identified patent and that said Letters Patent are hereby corrected as shown below:

Column 2, line 22, "hereiafter" should read -- hereinafter --;

Column 4, line 36, "perthyroidism. bicarbonate," should read -- perthyroidism. --;

Column 8, line 54, "-$CH_2Ch_2$-;" should read -- -$CH_2CH_2$-; --;

Column 9, line 25, "-C≡$CH_2$-$(CH_2)_g$-$CH_2$-," should read -- -C≡C-$CH_2$-$(CH_2)_g$-$CH_2$-, --;

Column 12, line 40, "prostagland analogs" should read -- prostaglandin analogs --; line 44, "13,14-dihydro-$PGE_1$" should read -- 13,14-didehydro-$PGE_1$ --; line 60, "cycloalky," should read -- cycloalkyl, --;

Column 13, line 36, "(o-, m-, or p-methoxyphenyl," should read -- (o-, m-, or p-)methoxyphenyl, --; line 37, "4- or 5-)chloro-" should read -- (4- or 5-)chloro- --;

Column 14, line 6, "pG analogs" should read -- PG analogs --; line 48, "free acid for," should read -- free acid form,--;

Column 15, line 9, "ethylenediaine," should read -- ethylenediamine, --;

Column 18, lines 24-25, "2-, 3-, or 4-)-" should read -- (2-, 3-, or 4-)- --;

Column 25, after formula XXXIII an arrow ↓ should appear;

Column 33, line 30, "-$(CH_2)_3$-$(CH_2)_g$-$(R_2)_2$-," should read -- -$(CH_2)_3$-$(CH_2)_g$-$C(R_2)_2$-, --; line 42, "XXXIVIII" should read -- XXXVIII --;

Column 34, lines 38-39, "dichorophenoxy-, (4- or 6-chloro-" should read -- dichlorophenoxy-, (4- or 6-)chloro- --;

Column 35, line 6, "o-, or p-)methylphenyl-" should read -- (o-, m-, or p-)methylphenyl- --;

Column 36, line 59, "the ester, a 3α or 3β-" should read -- the corresponding 3α or 3β- --;

UNITED STATES PATENT OFFICE
CERTIFICATE OF CORRECTION

Patent No. 4,060,534　　　　　　　　　Dated 29 November 1977

Inventor(s) Gordon L. Bundy

It is certified that error appears in the above-identified patent and that said Letters Patent are hereby corrected as shown below:

Column 37, line 1, "udesirable" should read -- undesirable --;

Column 38, line 37, "XXXv" should read -- XXXV --;

Column 42, line 24, "formula LXII" should read -- formula LXIII --;

Column 49, line 62, "2β-carboxadehyde-1α-" should read -- 2β-carboxaldehyde-1α- --;

Column 50, line 41, "100 C." should read -- 100° C. --;

Column 51, line 50, "-5° C." should read -- -15° C. --;

Column 52, line 33, "δ]lactol" should read -- lactol --; line 34, "bistetrahydropyranyl" should read -- bis-tetrahydropyranyl --; line 46, "ae" should read -- are --.

Column 56, line 4, "9-methoxy-$PGF_1$" should read -- 9-methylene-$PGF_1$ --;

Column 57, line 27, "$R_2$ and $R_4$" should read -- $R_3$ and $R_4$ --;

Column 61, line 39, "$R_8$ is hydrogen," should read -- $R_8$ is hydroxy, --;

Column 62, line 23, "th" should read -- the --;

UNITED STATES PATENT OFFICE

CERTIFICATE OF CORRECTION

Patent No. 4,060,534      Dated 29 November 1977

Inventor(s) Gordon L. Bundy

It is certified that error appears in the above-identified patent and that said Letters Patent are hereby corrected as shown below:

Column 63, lines 33-35, " [structure with $R_3$ $R_4$] " should read -- [structure with $R_3$ $R_4$] --;

line 52, "$-CH_2-C\equiv C-(CH_2)_g-CH_2-$," should read -- 8. $-CH_2-C\equiv C-(CH_2)_g-CH_2-$, --;

Column 64, line 1, "13,14dihydro-" should read -- 13,14-dihydro- --; line 4, "$-CH_2 13$" should read -- $-CH_2-$. --; line 60, "ar" should read -- are --;

Column 65, line 5, "9-methylene 13,14dihydro" should read -- 9-methylene-13,14-dihydro --;

Column 66, line 3, "according to to" should read -- according to --; line 4, "at leat" should read -- at least --.

Signed and Sealed this

Thirtieth Day of September 1980

[SEAL]

Attest:

SIDNEY A. DIAMOND

Attesting Officer     Commissioner of Patents and Trademarks